US012578288B2

(12) United States Patent
Papillon

(10) Patent No.: US 12,578,288 B2
(45) Date of Patent: Mar. 17, 2026

(54) METHODS AND SYSTEMS FOR ALUMINUM FILTRATION DETECTION

(71) Applicant: GE Precision Healthcare LLC, Waukesha, WI (US)

(72) Inventor: Stéphane Papillon, Seine et Marne (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 227 days.

(21) Appl. No.: 18/437,061

(22) Filed: Feb. 8, 2024

(65) Prior Publication Data

US 2025/0258111 A1     Aug. 14, 2025

(51) Int. Cl.
    *G01N 23/04*      (2018.01)
    *G01N 23/083*    (2018.01)
    *A61B 6/04*       (2006.01)

(52) U.S. Cl.
    CPC ........... *G01N 23/04* (2013.01); *G01N 23/083* (2013.01); *A61B 6/0407* (2013.01); *G01N 2223/505* (2013.01)

(58) Field of Classification Search
    CPC ................ G01N 23/04; G01N 23/083; G01N 2223/505; A61B 6/0407; A61B 6/4441
    See application file for complete search history.

(56) References Cited

U.S. PATENT DOCUMENTS

| | | | |
|---|---|---|---|
| 5,687,210 A | 11/1997 | Maitrejean et al. | |
| 5,928,459 A | 7/1999 | Geyer et al. | |
| 7,597,476 B2 * | 10/2009 | Neumann ............... | A61B 6/542 |
| | | | 378/207 |

FOREIGN PATENT DOCUMENTS

EP          0678191 B1     2/2001

OTHER PUBLICATIONS

Cranley, K. et al., "Catalogue of Diagnostic X-ray Spectra and Other Data (IPEM Report 78)," Radiology, vol. 4, No. 3, Aug. 1998, 2 pages.

* cited by examiner

*Primary Examiner* — Courtney D Thomas
(74) *Attorney, Agent, or Firm* — McCoy Russell LLP

(57) ABSTRACT

Various methods and systems are provided for X-ray imaging systems. In one example, a method for measuring an equivalent aluminum filtration of a tabletop comprises acquiring a single X-ray image of a tabletop and an aluminum filtration scale using a detector; identifying a brightness of the tabletop and a brightness of the aluminum filtration scale in the single X-ray image; computing an aluminum equivalence of the tabletop, converting the brightness of the aluminum filtration scale to an air KERMA of the aluminum filtration scale and converting the aluminum equivalence of the tabletop to an air KERMA of the tabletop; and comparing the air KERMA of the tabletop to the air KERMA of the aluminum filtration scale to identify an air equivalent aluminum filtration of the tabletop.

20 Claims, 13 Drawing Sheets

FIG. 3A

| Case | Foam Density (kg/m3) | Carbon Skin Thick (mm) |
|---|---|---|
| 13 | 51 | 0.5 |
| 14 | 51 | 1 |
| 15 | 51 | 2 |
| 16 | 61 | 0.5 |
| 17 | 61 | 1 |
| 18 | 61 | 2 |
| 19 | 71 | 0.5 |
| 20 | 71 | 1 |
| 21 | 71 | 2 |
| 46 | 81 | 0.5 |
| 47 | 81 | 1 |
| 48 | 81 | 2 |

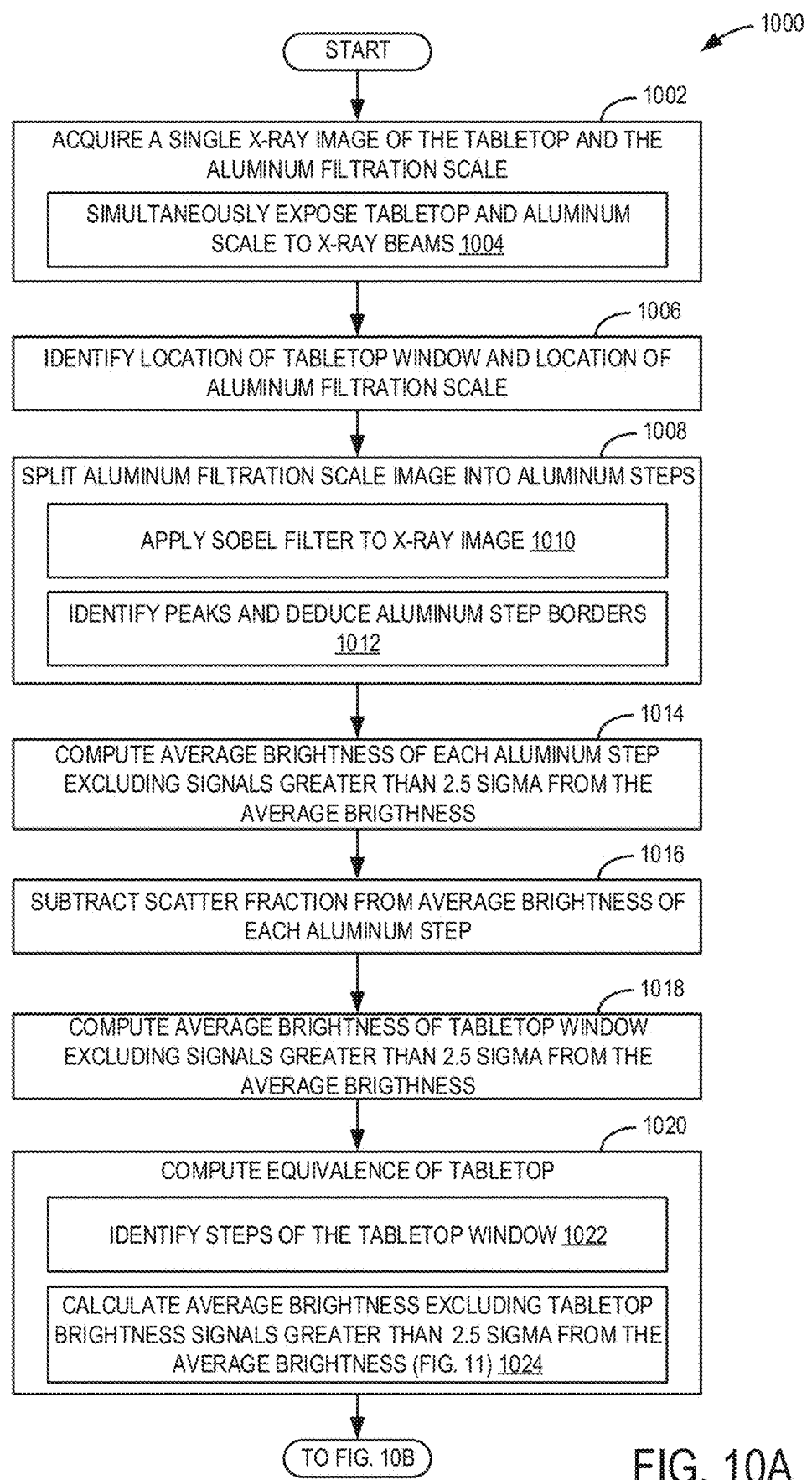

1000

START

1002

ACQUIRE A SINGLE X-RAY IMAGE OF THE TABLETOP AND THE ALUMINUM FILTRATION SCALE

SIMULTANEOUSLY EXPOSE TABLETOP AND ALUMINUM SCALE TO X-RAY BEAMS 1004

1006

IDENTIFY LOCATION OF TABLETOP WINDOW AND LOCATION OF ALUMINUM FILTRATION SCALE

1008

SPLIT ALUMINUM FILTRATION SCALE IMAGE INTO ALUMINUM STEPS

APPLY SOBEL FILTER TO X-RAY IMAGE 1010

IDENTIFY PEAKS AND DEDUCE ALUMINUM STEP BORDERS 1012

1014

COMPUTE AVERAGE BRIGHTNESS OF EACH ALUMINUM STEP EXCLUDING SIGNALS GREATER THAN 2.5 SIGMA FROM THE AVERAGE BRIGTHNESS

1016

SUBTRACT SCATTER FRACTION FROM AVERAGE BRIGHTNESS OF EACH ALUMINUM STEP

1018

COMPUTE AVERAGE BRIGHTNESS OF TABLETOP WINDOW EXCLUDING SIGNALS GREATER THAN 2.5 SIGMA FROM THE AVERAGE BRIGTHNESS

1020

COMPUTE EQUIVALENCE OF TABLETOP

IDENTIFY STEPS OF THE TABLETOP WINDOW 1022

CALCULATE AVERAGE BRIGHTNESS EXCLUDING TABLETOP BRIGHTNESS SIGNALS GREATER THAN 2.5 SIGMA FROM THE AVERAGE BRIGHTNESS (FIG. 11) 1024

METHODS AND SYSTEMS FOR ALUMINUM FILTRATION DETECTION

FIELD

Embodiments of the subject matter disclosed herein relate to medical imaging systems, and more particularly, to radiographic imaging systems.

BACKGROUND

Radiographic imaging systems may be used in various applications, including medical and industrial applications. In a medical environment, a radiographic imaging device may provide a non-invasive means of imaging tissue and bone of a patient. The radiographic imaging device may have the capability of capturing multiple images at designated intervals and displaying the images in a sequence to create a single image of the object being examined.

The radiographic imaging device may be an X-ray imaging device comprised of a C-arm coupled to a base unit. The C-arm may include an X-ray source positioned at one end of the arm and a detector positioned at another end of the arm. A clearance may be provided between the X-ray source and the detector to receive an object, such as a portion of the patient's body, which may be irradiated with radiation from the X-ray source. At least a portion of the patient's body may be positioned on a tabletop of the X-ray imaging device, which may be at least partially positioned in the clearance of the C-arm between the X-ray source and the detector. Upon irradiating the object, the X-ray radiation penetrates through the object and the tabletop, and is captured by the detector. By penetrating the object and the tabletop placed between the X-ray source and detector, the X-rays enable an image of the object to be captured and relayed to the display monitor, where the image may be displayed or stored and retrieved later. The image of the object may further include the portion of the tabletop positioned between the X-ray source and the detector.

BRIEF DESCRIPTION

In one example, a method for measuring an equivalent aluminum filtration of a tabletop comprising: acquiring a single X-ray image of a tabletop and an aluminum filtration scale using a detector; identifying a brightness of the tabletop and a brightness of the aluminum filtration scale in the single X-ray image; computing an aluminum equivalence of the tabletop, converting the brightness of the aluminum filtration scale to an air kinetic energy released per unit mass (KERMA) of the aluminum filtration scale; converting the aluminum equivalence of the tabletop to an air KERMA of the tabletop; and comparing the air KERMA of the tabletop to the air KERMA of the aluminum filtration scale to identify an air equivalent aluminum filtration of the tabletop. The tabletop may be a tabletop of a patient bed or other surface that a patient or imaging subject is positioned on. For example, the tabletop may be a patient bed of a medical X-ray imaging system.

The method for measuring the equivalent aluminum filtration of the tabletop may be executed using an X-ray imaging system comprising an X-ray tube, a detector, and an aluminum filtration measurement tool having a tabletop window and the aluminum filtration scale. The X-ray imaging system may be configured for manufacturing and quality control purposes, and not for medical imaging of a patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

Figure 3A:
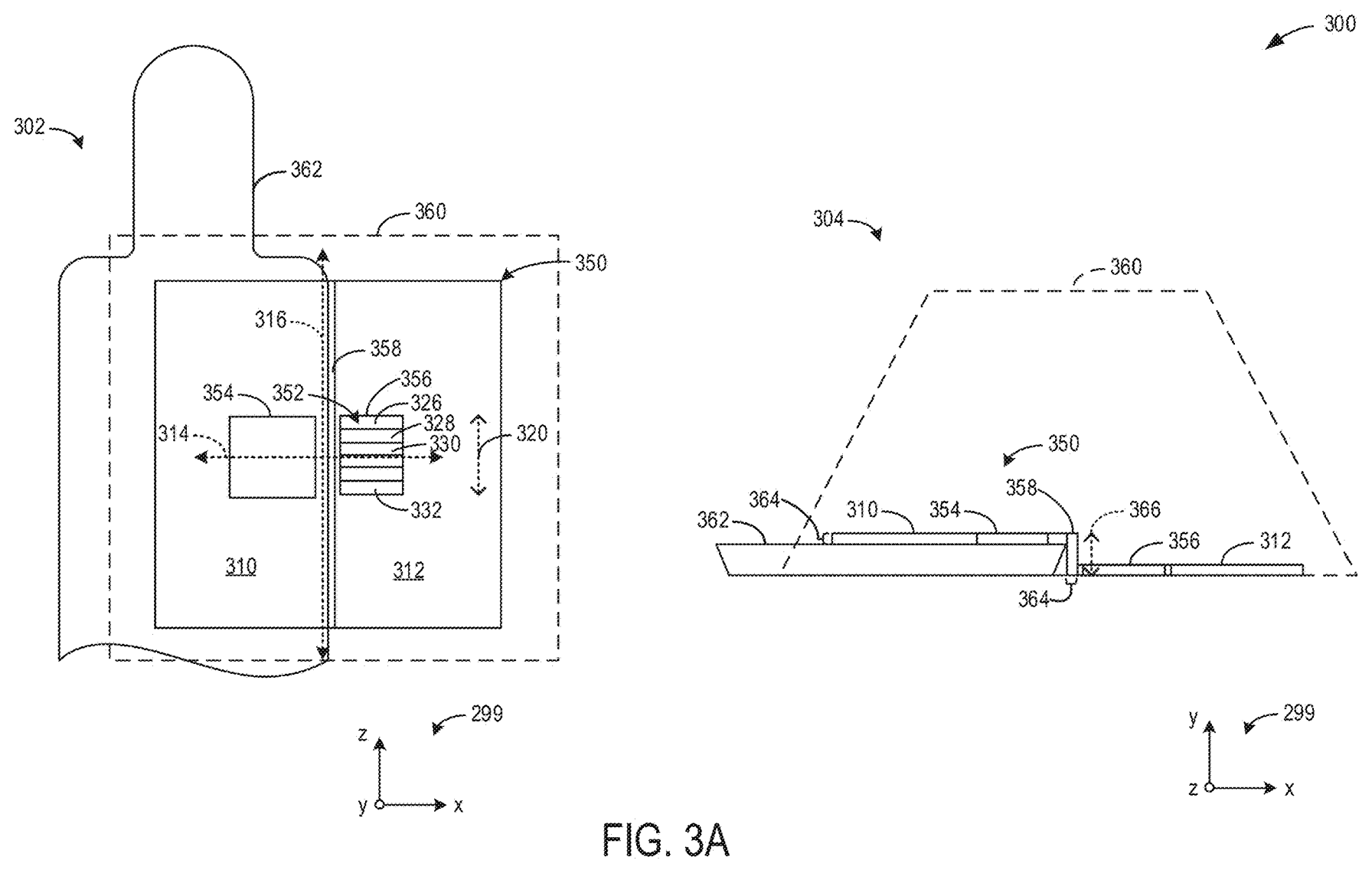

FIGS. 3A-3B show views of an example aluminum filtration measurement tool, including an aluminum filtration scale, according to an embodiment;

FIGS. 10A-10B show a flow chart of a method for measuring an equivalent aluminum filtration of a tabletop.

DETAILED DESCRIPTION

Figure 2:
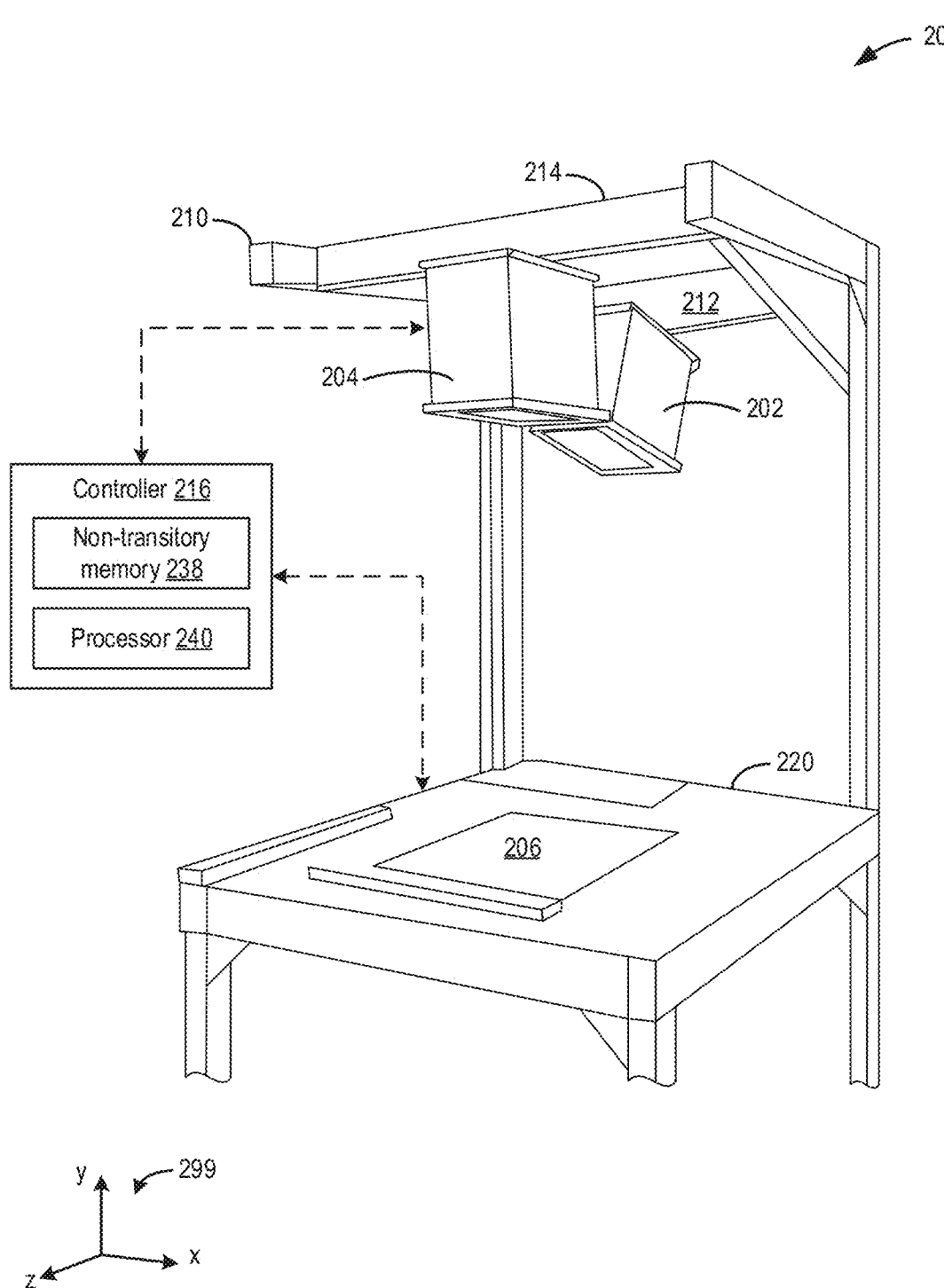
FIG. 2 shows an example X-ray imaging system, according to an embodiment.
Figure 3B:
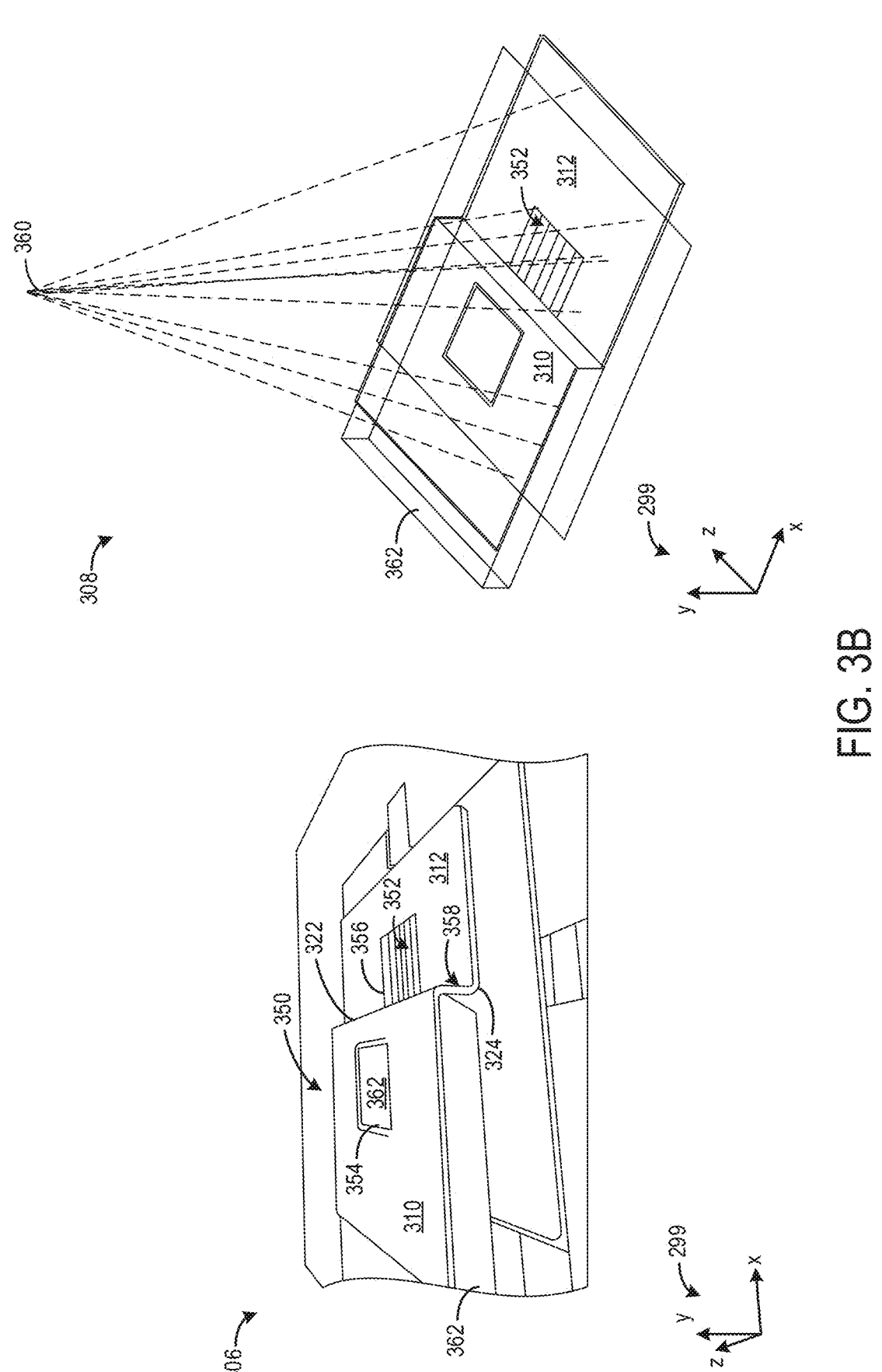
Figure 4:
FIG. 4 shows an example image captured of a tabletop and of the aluminum filtration measurement tool of FIGS. 3A-3B by the X-ray imaging system of FIG. 2.
Figure 5:
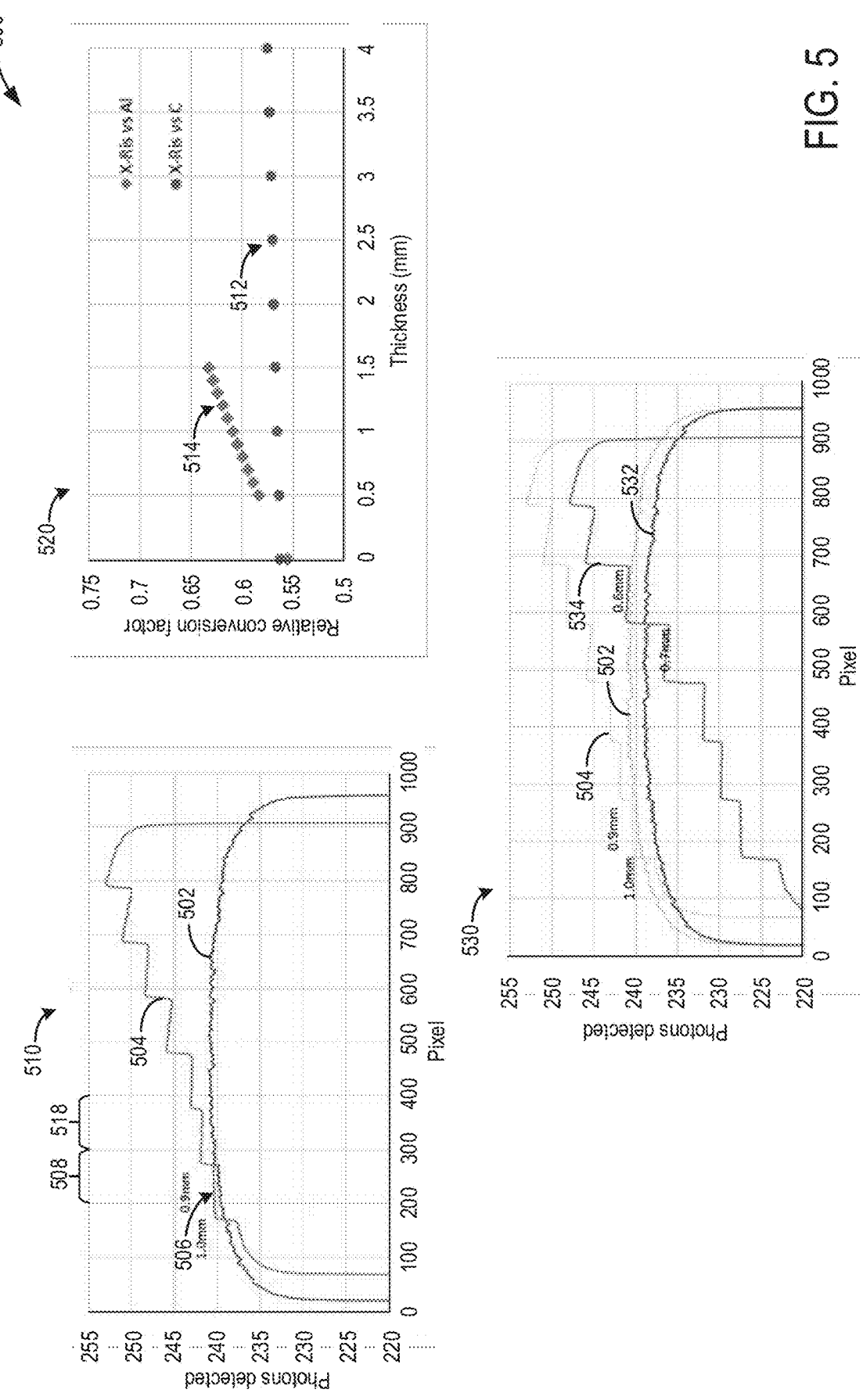
FIG. 5 shows a first series of graphs illustrating application of conversion factors (CF) to cesium iodide (CsI) scintillator profiles of the aluminum filtration scale and the tabletop of FIG. 4 to compute air KERMA profiles thereof, according to an embodiment.
Figure 6:
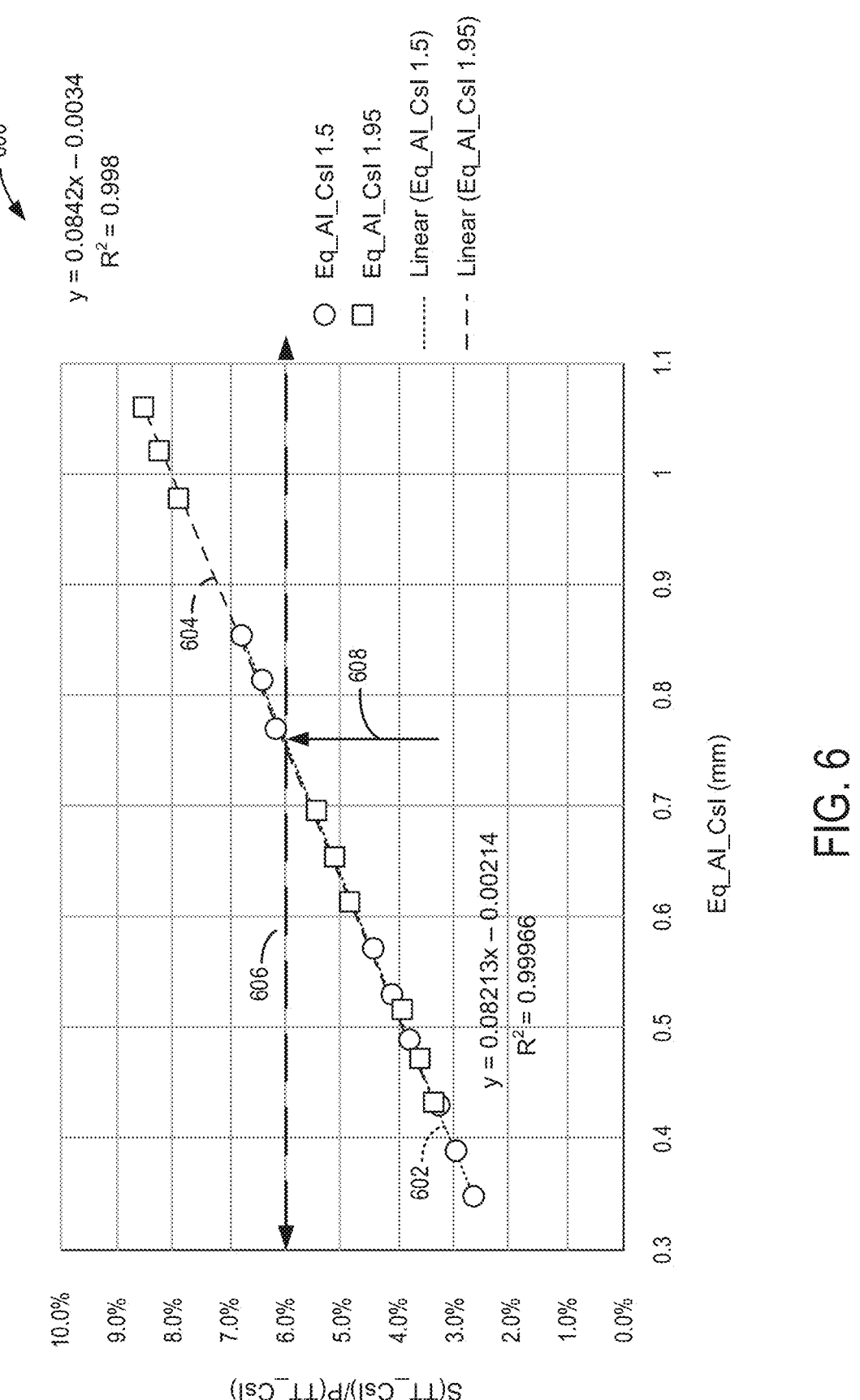
FIG. 6 shows a graph with plots illustrating tabletop CsI scatter correction, according to an embodiment.
Figure 7:
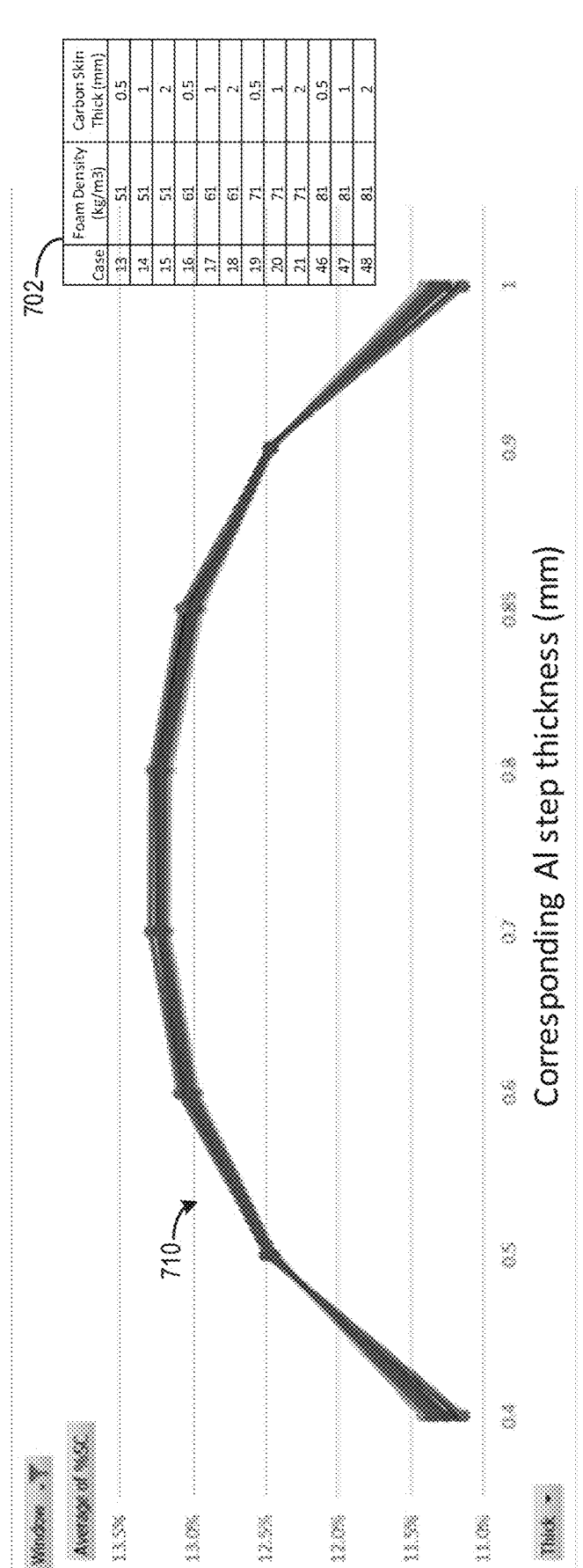
FIG. 7 shows a graph with plots illustrating an effect of a scatter point spread function (ScPCF) that provides a scattered signal shape over an irradiated area of the tabletop, according to an embodiment.
Figure 8:
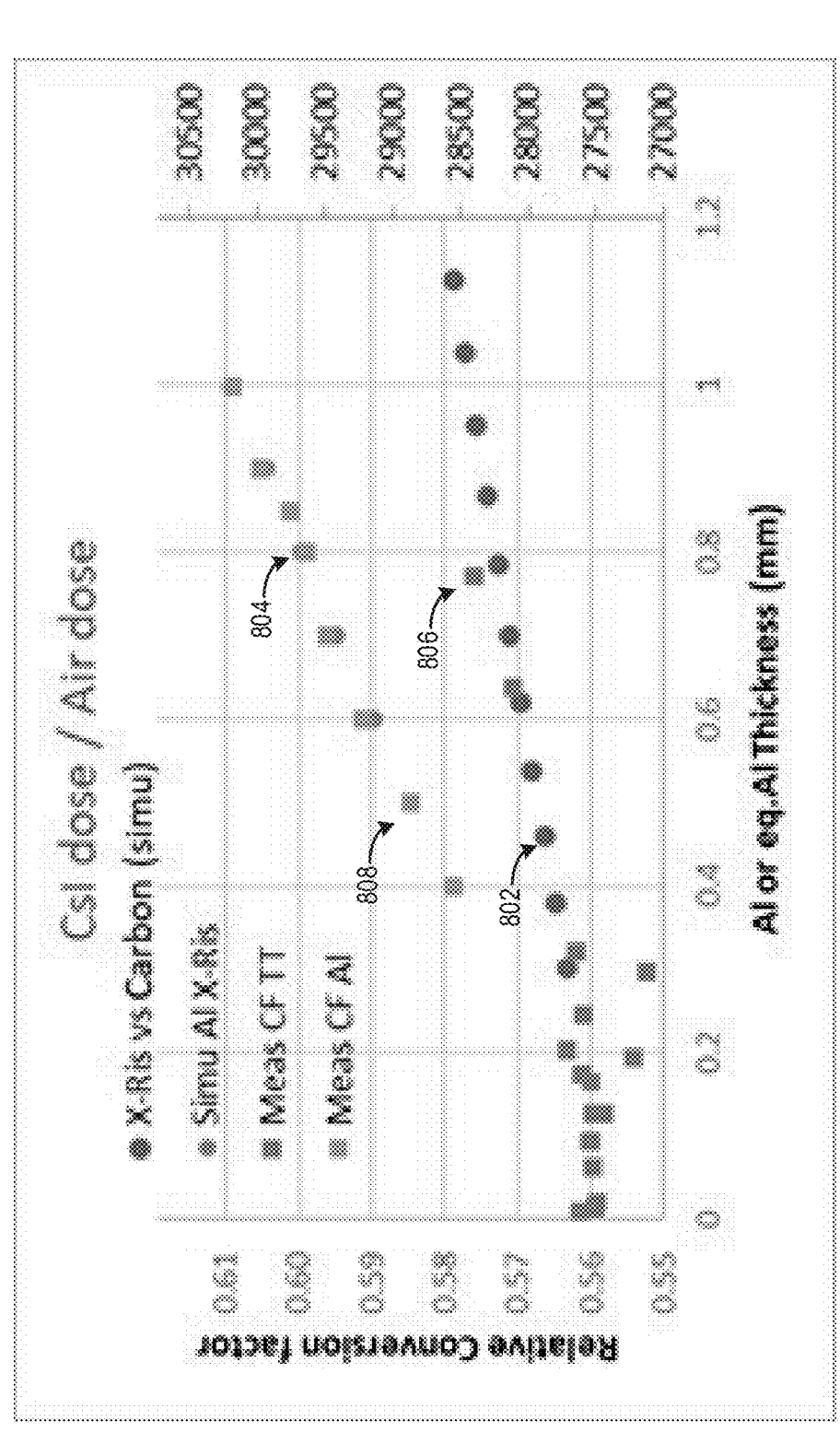
FIG. 8 shows a graph with plots illustrating relative CF for aluminum or equivalent aluminum thicknesses of the aluminum filtration scale and the tabletop, according to an embodiment.
Figure 9:
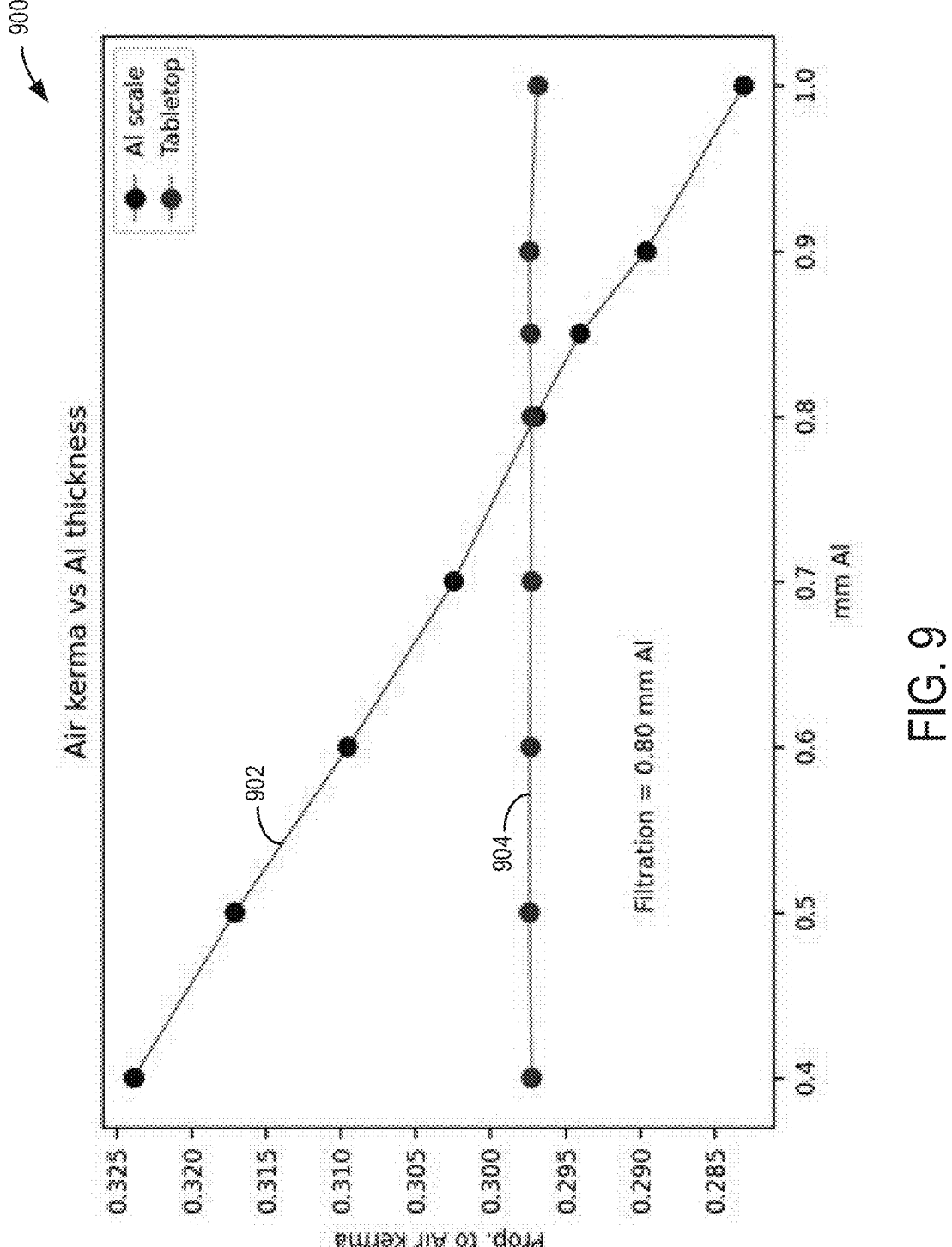
FIG. 9 shows a graph with plots illustrating air KERMA vs aluminum thickness filtration profiles of the aluminum filtration scale and the tabletop, according to an embodiment.
Figure 10B:
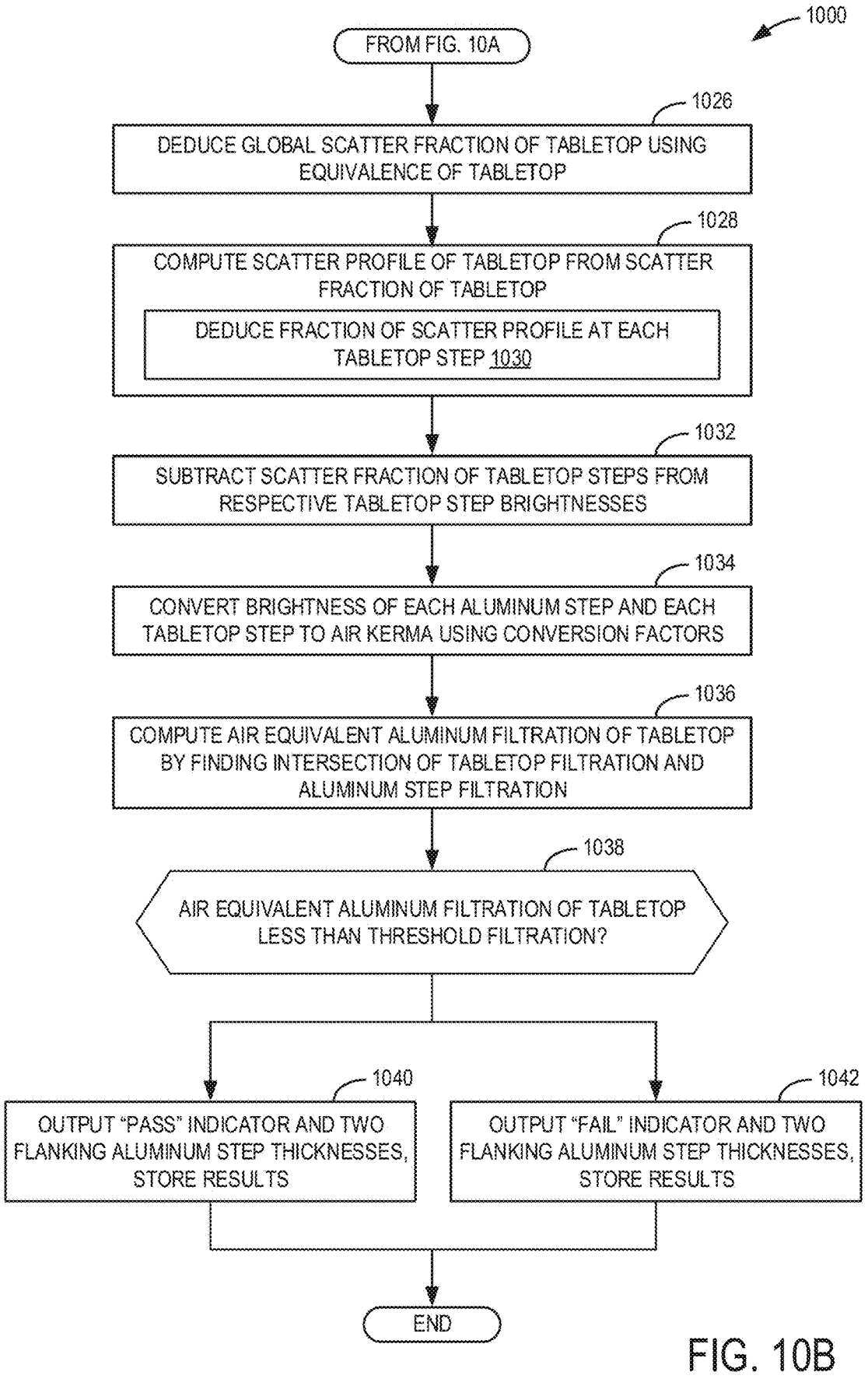
Figure 11:
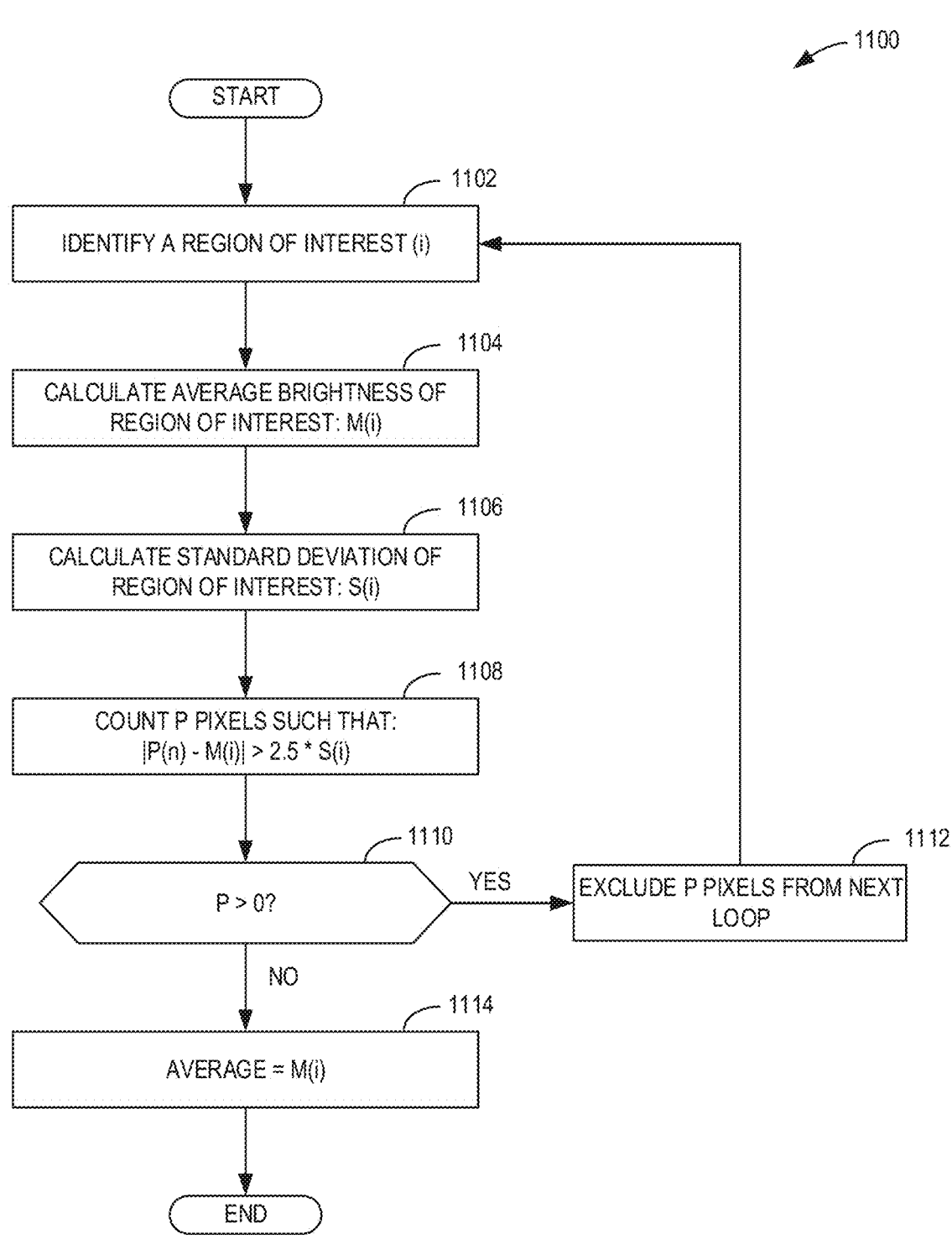
FIG. 11 shows a flow chart of a method for performing an iterative cleanup of individual pixels of the tabletop window in an X-ray image.

The following description relates to various embodiments for identifying an aluminum equivalence filtration measurement of a tabletop. The tabletop may be a surface of a medical imaging system, such as the medical imaging system of FIG. 1, on which an imaging subject is positioned. Irradiating beams of the medical imaging system of FIG. 1 may pass through the imaging subject and be filtered by the tabletop on a path to a detector of the medical imaging system. The aluminum equivalence filtration measurement of the tabletop of FIG. 1 may provide a measurement of the amount of filtration provided by the tabletop. The aluminum equivalence filtration measurement of the tabletop may be performed using a non-medical X-ray imaging system, an example of which is shown in FIG. 2. An example aluminum filtration tool, including a tabletop window and an aluminum filtration scale, is shown in FIGS. 3A-3B. The aluminum filtration tool may be positioned on the tabletop and a detector of the non-medical X-ray imaging system of FIG. 2, and the tabletop and the aluminum filtration scale may be simultaneously exposed to a single X-ray beam to capture an X-ray image, an example of which is shown in FIG. 4. Information from the X-ray image of FIG. 4 may be used to determine the aluminum equivalence filtration measurement of the tabletop, as described with respect to FIGS. 5-9. FIG. 5 shows a first series of graphs illustrating application of conversion factors (CF) to cesium iodide (CsI) scintillator profiles of the aluminum filtration scale and the tabletop of FIG. 4 to compute air KERMA profiles thereof. FIG. 6 shows a graph with plots illustrating tabletop CsI scatter correction. FIG. 7 shows a graph with plots illustrating an effect of a scatter point spread function (ScPCF) that provides a scattered signal shape over an irradiated area of the tabletop. FIG. 8 shows a graph with plots illustrating relative CFs for aluminum or equivalent aluminum thicknesses of the aluminum filtration scale and the tabletop. FIG. 9 shows a graph with plots illustrating air KERMA vs aluminum thickness filtration profiles of the aluminum filtration scale and the tabletop. FIGS. 10A-10B show a flow chart of a method for measuring an equivalent aluminum filtration of a tabletop. FIG. 11 provides further detail of the method 1000 and shows a method 1100 for performing an iterative cleanup of individual pixels of the tabletop window in the X-ray image. FIGS. 2-3B are shown approximately to scale.

Figure 1:
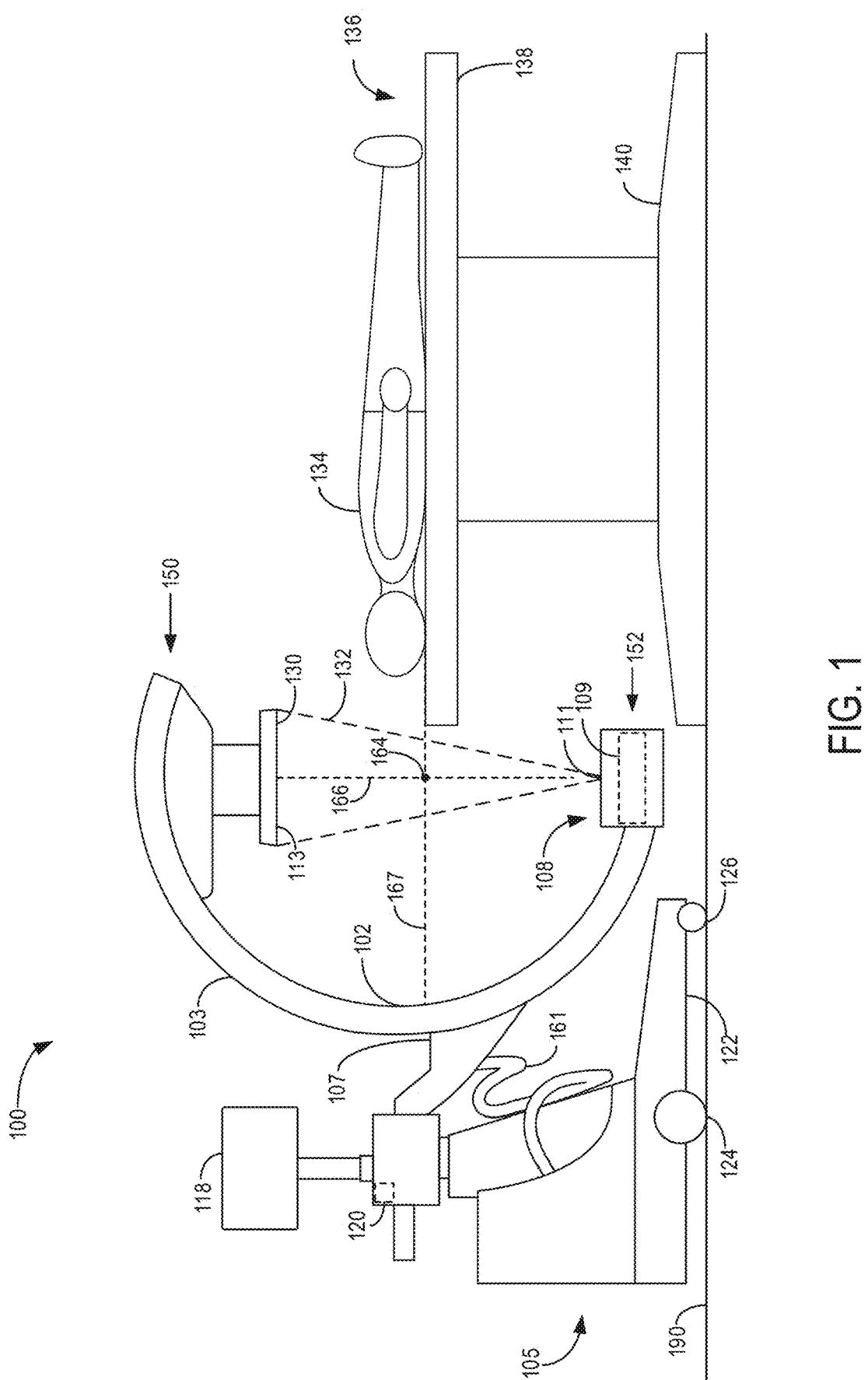
FIG. 1 shows an example medical imaging system including a C-arm, according to an embodiment.

Referring to FIG. 1, an imaging system 100 including a C-arm 102 (which may be referred to herein as a C-shaped gantry) is schematically shown. Imaging system 100 may be referred to herein as a medical imaging system and/or C-arm imaging system. The imaging system 100 includes a radiation source, and in the examples described herein, the radiation source is an X-ray unit 108 (which may be referred to herein as an X-ray tube) positioned opposite to detector 130 (which may be referred to herein as an X-ray detector) and configured to emit X-ray radiation. In other examples, the radiation source may be configured to emit a different type of radiation for imaging (e.g., imaging a subject, such as patient 134), such as gamma rays, and the detector (e.g., X-ray detector 130) may be configured to detect the radiation emitted by the radiation source (e.g., X-ray beam 132). The imaging system 100 additionally includes base unit 105 supporting imaging system 100 on ground surface 190 on which the imaging system 100 sits (e.g., via base 122 supported by wheel 124, wheel 126, etc.).

The C-arm 102 includes a C-shaped portion 103 connected to an extended portion 107, with the extended portion 107 rotatably coupled to the base unit 105. The detector 130 is coupled to the C-shaped portion 103 at a first end 150 of the C-shaped portion 103, and the X-ray unit 108 is coupled to the C-shaped portion 103 at an opposing end, such as a second end 152 of the C-shaped portion 103. As an example, the C-arm 102 may be configured to rotate at least 180 degrees in opposing directions relative to the base unit 105. The C-arm 102 is rotatable about at least a rotational axis 164 and may additionally rotate about axis 167. The C-shaped portion 103 may be rotated as described above in order to adjust the X-ray unit 108 and detector 130 (positioned on opposite ends of the C-shaped portion of the C-arm 102 along axis 166, where axis 166 intersects rotational axis 164 and extends radially relative to rotational axis 164) through a plurality of positions.

During an imaging operation (e.g., a scan), a portion of a body of a patient placed in an opening formed between the X-ray unit 108 and detector 130 may be irradiated with radiation from the X-ray unit 108. For example, patient 134 may be supported by a patient support table 136, with the patient support table 136 including a support surface 138 and base 140, and may be arranged between the X-ray unit 108 and the detector 130. The X-ray unit 108 includes an X-ray tube insert 109 and X-ray radiation generated by the X-ray tube insert 109 may emit from the X-ray unit 108. The radiation may penetrate the portion of the body arranged to be irradiated and may travel to the detector 130 where the radiation is captured (e.g., intercepted by a detector surface 113 of the detector 130). By penetrating the portion of the body placed between the X-ray unit 108 and detector 130, an image of the body is captured and relayed to an electronic controller 120 of the imaging system 100 (e.g., via an electrical connection line, such as electrically conductive cable 161). The image may be displayed via display device 118. Images of the subject acquired by the imaging system 100 via the X-ray unit 108 and the detector 130 as described above may be referred to herein as projection images and/or scan projection images.

The base unit 105 may include the electronic controller (e.g., a control and computing unit) that processes instructions or commands sent from the user input devices during operation of the imaging system 100. The base unit 105 may also include an internal power source (not shown) that provides electrical power to operate the imaging system 100. Alternatively, the base unit 105 may be connected to an external electrical power source to power the imaging system 100. A plurality of connection lines (e.g., electrical cables, such as electrically conductive cable 161) may be provided to transmit electrical power, instructions, and/or data between the X-ray unit 108, detector 130, and the control and computing unit. The plurality of connection lines may transmit electrical power from the electrical power source (e.g., internal and/or external source) to the X-ray unit 108 and detector 130.

The C-arm 102 may be adjusted to a plurality of different positions by rotation of the C-shaped portion 103 of the C-arm 102. For example, in an initial, first position shown by FIG. 1, the detector 130 may be positioned vertically above the X-ray unit 108 relative to a ground surface 190 on which the imaging system 100 sits, with axis 166 arranged normal to the ground surface 190 intersecting a midpoint of each of an outlet 111 of X-ray unit 108 and detector surface 113 of detector 130. The C-arm 102 may be adjusted from the first position to a different, second position by rotating the C-shaped portion 103. In one example, the second position may be a position in which the X-ray unit 108 and detector 130 are rotated 180 degrees together relative to the first position, such that the X-ray unit 108 is positioned vertically above the detector 130, with axis 166 intersecting the midpoint of the outlet 111 of the X-ray unit 108 and the midpoint of the detector surface 113 of the detector 130. When adjusted to the second position, the X-ray unit 108 may be positioned vertically above the rotational axis 164 of the C-shaped portion 103 of the C-arm 102, and the detector 130 may be positioned vertically below the rotational axis 164. Different rotational positions of the C-arm 102 are possible.

During irradiation of an imaging subject (e.g., the patient 134), radiation emitted by the radiation source of a medical imaging system (e.g., the imaging system 100) may pass through the imaging subject and through a tabletop (e.g., the support surface 138) of the imaging system before being received by the detector (e.g., the detector 130). In passing through the tabletop, characteristics of the irradiating beams (e.g., the X-ray beam 132), such as a beam strength, may be changed by material properties of the tabletop. For example, the irradiating beam may experience inherent filtration when passing through the tabletop on the path to the detector. Inherent filtration of the irradiating beam by the tabletop may remove lower energy beams from the irradiating beam by absorbing lower energy photons of the irradiating beam into the tabletop. Filtration of the irradiating beam by the tabletop may affect measurements by the detector. For example, an image generated from image data captured by the detector may have low contrast, low sharpness, and/or low brightness, depending on an amount of filtration by the tabletop, compared to an image generated from non-filtered irradiating beam image data. It is desirable to characterize material properties of the tabletop, and use information about the material properties to adjust measurements captured by the detector.

Spectral filtration of X-ray beams is used to supplement filtration in some irradiation imaging systems. For example, an aluminum filter having a known thickness may be positioned between an irradiating source and a detector. Filtration of an X-ray beam emitted by the irradiating source is increased (e.g., energy of the X-ray beam that reaches the detector is decreased) with an increase in the thickness of the aluminum filter. Filtration of an irradiating beam by a tabletop, which may or may not include aluminum, may be modeled by comparing tabletop filtration to aluminum filtration. For example, an aluminum equivalent filtration measurement of the tabletop may be identified and corresponding adjustments may be made to measurements captured by the detector to achieve accurate measurements and imaging data. Conventionally, an aluminum equivalent filtration measurement is performed by human interpretation of a developed radiographic film. Radiographic film technology is progressively being used less often in diagnostic X-ray, and is expected to become obsolete. Additionally, a time to develop film may be undesirably long compared to a digital X-ray image, which may be available less than one minute after X-ray exposure. Thus, a method is desired for identifying an aluminum equivalence filtration measurement of a tabletop that is more accurate, faster, and less resource intensive, compared to conventional radiographic methods.

Described herein is a method for aluminum filtration equivalence measurement. The method comprises acquiring a single X-ray image of a tabletop and an aluminum filtration scale captured using a detector, identifying a brightness of the tabletop and a brightness of the aluminum filtration scale in the single X-ray image, computing an aluminum equivalence of the tabletop, converting the brightness of the aluminum filtration scale to an air KERMA of the aluminum filtration scale, converting the aluminum equivalence of the tabletop to an air KERMA of the tabletop, and comparing the air KERMA of the tabletop to the air KERMA of the aluminum filtration scale to identify an air equivalent aluminum filtration of the tabletop. The method further includes performing scatter correction on the brightness of the aluminum filtration scale and on the aluminum equivalence of the tabletop.

FIG. 2 shows an example X-ray imaging system 200. The imaging system 200 may be an embodiment of an X-ray imaging system, and may thus include one or more of the same elements as the medical imaging system 100 of FIG. 1. However, where the medical imaging system 100 is configured to capture medical X-ray images of imaging subjects (e.g., a patient), the X-ray imaging system 200 is configured as a manufacturing and quality control tool. For example, the X-ray imaging system 200 may be used to capture X-ray images of inanimate objects, such as a tabletop and/or a tabletop sample, and assess material qualities of the tabletop. An axis system 299 is provided in FIGS. 2-4 for reference. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples.

The imaging system 200 is configured with a vertical X-ray tube 204 and a radiology digital X-ray detector 206, herein also "the detector". In some embodiments, the imaging system 200 is further configured with an inclined X-ray tube 202. The vertical X-ray tube 204 and the inclined X-ray tube 202 may each be mounted on one of two crossbars 214, 212 of a frame 210 of the imaging system 200. Each of the vertical X-ray tube 204 and the inclined X-ray tube 202 may be moveable along a respective crossbar of the two crossbars 214, 212. For example, the vertical X-ray tube 204 may be repositioned (e.g., moved/slid) on the crossbar 214 along the x-axis to assist in focusing an X-ray beam on a desired region of the detector 206 (and an object positioned thereon for imaging). In further embodiments, one or more of the vertical X-ray tube 204 and the inclined X-ray tube 202 may be moveable in three dimensions, for example, as enabled by adjustable elements of the two crossbars 214, 212, and/or the frame 210 of the imaging system 200. In some embodiments, the vertical X-ray tube 204 may be rotatable (e.g., by 90 degrees) to provide a constant beam quality for comparing regions of interest in an aluminum scale and tabletop window, as further described with respect to FIGS. 3A-10B. Additionally, a position of the detector 206 may be adjustable with respect to one or more of the x-axis, the y-axis, and the z-axis. The X-ray imaging system 200 may be mobile, for example, the frame 210 of the X-ray imaging system 200 may be configured with wheels (not shown in FIG. 2) that enable the imaging system 200 to be moved about a space, such as throughout a manufacturing environment.

The vertical X-ray tube 204 is configured to direct irradiating X-ray beams in a direction orthogonal to the detector 206 during an imaging operation (e.g., an imaging scan). As further described herein with respect to FIGS. 3A-4 and 10A-10B, the X-ray beam may penetrate a portion of a tabletop and an aluminum filtration measurement tool positioned between the vertical X-ray tube 204 and the detector 206. Penetrating X-ray beams travel to the detector 206, where the radiation is captured by the detector 206. The detector 206 may be any type of X-ray detector. For example, the radiology digital X-ray detector 206 may comprise a flat panel (e.g., in the x-z plane) and a cesium iodide (CsI) scintillator, for example. The CsI scintillator of the detector 206 is configured to receive X-ray beams (e.g., from the vertical X-ray tube 204) and convert the X-ray beams to visible light. The detector 206 may detect and capture the visible light as image data. In other examples, the detector 206 may include a different type of scintillator, or may not include a scintillator-like direct conversion detector. The method is described herein with respect to a CsI scintillator detector, and other types of X-ray detectors may be used as the detector 206 without departing from the scope of the present disclosure.

The imaging system 200 is further configured with a controller 216, which may be an embodiment of the electronic controller 120 of FIG. 1. The controller 216 is communicably coupled to the vertical X-ray tube 204, the inclined X-ray tube 202, the detector 206, and other elements of the imaging system 200 via wired or wireless connections. For example, the controller 216 may control one or more motors housed in a base 220 of the imaging system 200, where the one or more motors are configured to adjust a position of the detector 206, as further described herein. The controller 216 may further control emission of irradiating beams by the inclined X-ray tube 202 and/or by the vertical X-ray tube 204. The controller 216 includes a processor 240 configured to execute machine-readable instructions stored in a non-transitory memory 238 of the controller 216. The processor 240 may be single core or multi-core, and the programs executed by the processor 240 may be configured for parallel or distributed processing. In some embodiments, the processor 240 may optionally include individual components that are distributed through-out two or more devices, which may be remotely located and/or configured for coordinated processing. In some embodiments, one or more aspects of the processor 240 may be virtualized and executed by remotely-accessible net-worked computing devices configured in a cloud computing configuration. In some embodiments, the processor 240 may include other electronic components capable of carrying out processing functions, such as a digital signal processor, a field-programmable gate array (FPGA), or a graphics board. In some embodiments, the processor 240 may include mul-tiple electronic components capable of carrying out process-ing functions. For example, the processor 240 may include two or more electronic components selected from a plurality of possible electronic components, including a central pro-cessor, a digital signal processor, a field-programmable gate array, and a graphics board. In still further embodiments, the processor 240 may be configured as a graphical processing unit (GPU), including parallel computing architecture and parallel processing capabilities. In some embodiments, the controller 216 may be integrated in the imaging system 200 (e.g., housed in the base 220). In other embodiments, the controller 216 may be part of a computing device commu-nicably coupled to the imaging system 200.

As further described herein with respect to FIGS. 3A-10B, the controller 216 may execute instructions for carrying out a method for aluminum equivalent filtration measurement, based on instructions stored on a memory of the controller 216 and in conjunction with signals received from sensors of the imaging system 200, such as the radiology digital X-ray detector 206. For example, the controller 216 may receive image data from the detector 206 and generate an X-ray image from the image data.

As further described herein, a tabletop and/or a tabletop sample (not shown in FIG. 2) may be positioned on the radiology digital X-ray detector 206, and the method described herein for aluminum equivalent filtration mea-surement may be executed to measure an aluminum equiva-lent thickness of the tabletop. Briefly, a position of the vertical X-ray tube 204 and/or the detector 206 may be adjusted such that X-ray beams output by the vertical X-ray tubes 204 may travel to and be detected by the detector 206. The vertical X-ray tube 204 may output irradiating X-ray beams, and the irradiating X-ray beams may pass through and be filtered by the tabletop (not shown in FIG. 2). In the embodiment described herein, the vertical X-ray tube 204 is configured to emit an irradiating X-ray beam that meets Title 21 of the Code of Federal Regulations (21 CFR). For example, the vertical X-ray tube 204 may, with or without addition of supplemental irradiation beam filters coupled to the vertical X-ray tube 204, emit irradiating beams with a half value layer (HVL) greater than 3.6 millimeters (mm) for a 100 kilovolts peak of the X-ray beam. Further details regarding measuring an aluminum equivalent thickness of the tabletop using the X-ray imaging system 200 of FIG. 2 are described with respect to FIGS. 3A-4.

Turning to FIGS. 3A and 3B, illustrations 300 are shown of an aluminum filtration measurement tool 350. The illus-trations 300 of FIGS. 3A-3B include a top-down view 302, a side view 304, a first perspective view 306, and a second perspective view 308 for visualization of the tool 350. The aluminum filtration measurement tool 350 comprises a first planar surface 310 having a tabletop window 354 extending through a thickness 364 of the first planar surface 310, and a second planar surface 312 having an aluminum scale window 356 extending through a thickness 364 of the second planar surface 312. The thickness 364 of each of the first planar surface 310 and the second planar surface 312 may be equal, in some embodiments. For example, the thickness 364 of each of the first planar surface 310 and the second planar surface 312 may be 3 mm. The second planar surface 312 is offset from and coupled to the first planar surface 310 by a vertical wall 358 that is perpendicular to the first planar surface 310 and to the second planar surface 312. For example, the vertical wall 358 is coupled to the first planar surface 310 along a first edge 322 and is coupled to the second planar surface 312 along a second edge 324. The first edge 322 and the second edge 324 are thus in vertical alignment. The first planar surface 310 is therefore elevated above the second planar surface 312 by a height 366 of the vertical wall 358. Each of the first planar surface 310 and the second planar surface 312 extend away from the first edge 322 and the second edge 324, respectively, in opposite directions. A thickness 364 of the vertical wall 358 may be equal to the thickness 364 of the first planar surface 310 and the second planar surface 312, in some embodiments. The first planar surface 310, the second planar surface 312, and the vertical wall 358 may be formed of lead and/or a mixture of lead and carbon. The aluminum filtration measurement tool 350 further comprises an aluminum filtration scale 352 positioned in the aluminum scale window 356. The alumi-num filtration scale 352 comprises a series of aluminum steps arranged in parallel along a length 320 of the alumi-num filtration scale 352. Each step of the series of aluminum steps has a different aluminum thickness compared to other steps of the series of aluminum steps. For example, a first step 326 of the series of steps may have a first thickness, a second step 328 of the series of steps may have a second thickness, less than the first thickness, a third step 330 of the series of steps may have a third thickness, less than the second thickness, and so on. In embodiments where the aluminum filtration scale 352 has eight steps in the series of steps, the first thickness of the first step 326 may be 1 mm, the second thickness of the second step 328 may be 0.9 mm, the third thickness of the third step 330 may be 0.85 mm, a fourth thickness of a fourth step may be 0.8 mm, a fifth thickness of a fifth step may be 0.7 mm, a sixth thickness of a sixth step may be 0.6 mm, a seventh thickness of a seventh step may be 0.5 mm, and an eighth thickness of an eighth step may be 0.4 mm. In some embodiments, a last step of the series of steps (e.g., a sixth step 332 in the embodiment shown in FIGS. 3A-3B) may include a smallest feasible thickness, where the thickness of the sixth step 332 provides little to no filtration.

The tabletop window 354 and the aluminum scale win-dow 356 may be approximately the same size and shape, and may be positioned side-by-side, with portions of the first planar surface 310, the vertical wall 358, and the second planar surface 312 therebetween. Irradiating beams may pass through the aluminum filtration measurement tool 350 at the tabletop window 354. As there is no material positioned in the tabletop window 354, irradiating beams may pass through the tabletop window 354 without being filtered. Irradiating beams may additionally pass through the aluminum filtration measurement tool 350 at the aluminum filtration scale 352 positioned in the aluminum scale window 356. The irradiating beams that pass through the aluminum filtration scale 352 may be filtered by different amounts. For example, irradiating beams that pass through a greater aluminum thickness (e.g., the thickness 364 of the first step 326) may be more filtered than irradiating beams that pass through a lesser aluminum thickness (e.g., the thickness of the third step 330) of the aluminum filtration scale 352. The first planar surface 310, the second planar surface 312, and the vertical wall 358 are configured to block transmission of irradiating beams through the aluminum filtration measurement tool 350. For example, the vertical wall 358 may prevent cross-scattered radiation between the tabletop 362 and sides of the aluminum filtration scale 352.

The aluminum filtration measurement tool 350 may be used with an X-ray imaging system (e.g., the X-ray imaging system 200 of FIG. 2) to measure an equivalent aluminum filtration of the tabletop 362. The tabletop 362 may be a support surface on which an imaging subject is positioned for X-ray imaging (e.g., the support surface 138 of FIG. 1). The tabletop 362 may be formed of, for example, a foam material positioned between two carbon-fiber layers. In some embodiments, the tabletop 362 measured using the aluminum filtration measurement tool 350 may be a sample and/or a section of material used to form support surfaces. The following description of FIGS. 3A and 3B refers to and includes elements of the X-ray imaging system 200 of FIG. 2, though it is to be understood that the aluminum filtration measurement tool 350 may be used with other X-ray imaging systems in other embodiments.

The tabletop 362 (e.g., the tabletop sample or section) may be positioned on the detector 206 of the X-ray imaging system 200, and the aluminum filtration measurement tool 350 may be positioned to at least partially cover the tabletop 362. For example, the first planar surface 310 is in face-sharing contact with at least a portion of the tabletop 362, and a portion of the tabletop 362 is exposed to air at the tabletop window 354. The second planar surface 312 is in face-sharing contact with the detector 206. In some embodiments, the vertical wall 358 may be at least partially in contact with the tabletop 362. The tabletop 362 and the aluminum filtration measurement tool 350 are positioned with respect to an X-ray tube (e.g., the vertical X-ray tube 204 of FIG. 2) and the detector 206 such that irradiating beams 360 emitted by the X-ray tube may fully encompass the aluminum filtration measurement tool 350. The irradiating beams 360 may at least partially encompass the tabletop 362 and the detector 206. Further, the X-ray tube is oriented such that a cathode-anode axis 316 of the X-ray tube is orthogonal to a center line 314 of the tabletop window 354 and the aluminum scale window 356. In this way, positioning of the aluminum filtration measurement tool 350 may block irradiating beams from surfaces of the tabletop 362 other than a portion of the tabletop 362 exposed by the tabletop window 354.

As described with respect to FIG. 2, the detector 206 may include a CsI scintillator that converts captured irradiating beams to light, which is processed by the controller of the X-ray imaging system to generate an X-ray image. Turning briefly to FIG. 4, the figure shows an example annotated X-ray image 400 captured of the aluminum filtration measurement tool 350 and the tabletop 362. Elements of the annotated X-ray image 400 that are annotated (e.g., are not captured by the detector 206 and are added to the X-ray image by a post processing method) are noted. The annotated X-ray image 400 includes annotation of a first region 402 that encompasses the tabletop window 354 and a portion of the tabletop 362 visible through the tabletop window 354. The annotated X-ray image 400 further includes annotation of a second region 404 that encompasses the aluminum scale window 356 and the aluminum filtration scale 352 positioned in the aluminum scale window 356.

As described above, the aluminum filtration scale 352 includes the series of steps having different aluminum thicknesses, and each aluminum thickness may filter the X-ray beams by a different amount. Thus, in an X-ray image captured by the detector 206, each step of the series of aluminum steps may have a different brightness. In the annotated X-ray image 400, an image of the aluminum filtration scale 352 shows a gradient of X-ray beam filtration performed by the aluminum filtration scale 352. For example, the second region 404 shows detected X-ray beams that have been filtered by the first step 326 having the first thickness, the second step 328 having the second thickness, and so on. The thickness of each step of the series of steps decreases in a direction of an arrow 406. Consequently, as the thickness decreases, filtering of the X-ray beam by the step decreases. X-ray beams filtered by the first step 326 are subject to the most filtering (e.g., by the first, greatest thickness), and thus a brightness of the image of the first step 326 is relatively low. X-ray beams filtered by the second step 328 are subject to less filtering than X-ray beams filtered by the first step 326, and a brightness of the image of the second step 328 is greater than a brightness of the image of the first step 326. In embodiments where the thickness of the sixth step 332 provides little to no filtration of X-ray beams, the brightness of the approximately equivalent to brightness of an unfiltered surface. As shown in the first region 402, the image of the tabletop 362 captured in the tabletop window 354 may have a single brightness for the entirety of the tabletop 362.

FIG. 5 shows a first series of graphs 500 illustrating application of conversion factors (CF) to cesium iodide (CsI) scintillator profiles of the aluminum filtration scale 352 and the tabletop 362 to compute air KERMA profiles thereof. A first graph 510 shows plots of CsI detection profiles of an aluminum filtration scale and of a tabletop, where the CsI detection profiles have not had conversion factors applied thereto. The first graph 510 includes pixel values along the x-axis, which indicates a position on an X-ray image (e.g., the annotated X-ray image 400 of FIG. 4), and a number of photons detected along the y-axis, which indicates a brightness of the X-ray image. Thus, the first graph 510 illustrates relative brightness of the X-ray image in different regions of the tabletop and of the aluminum filtration scale. A second graph 520 shows plots of relative conversion factors for each of the CsI detection profile of the aluminum filtration scale and the CsI detection profile of the tabletop. A third graph 530 shows plots of CsI detection profiles of an aluminum filtration scale and of a tabletop, where the CsI detection profiles (e.g., shown in the second graph 520) have had conversion factors applied thereto.

As described above, the CsI scintillator of the detector 206 is configured to convert radiation to visible light. A CsI detection profile may be generated for each of the tabletop 362 and the aluminum filtration scale 352 using visible light image data captured by the detector 206 via the CsI scintillator. The CsI detection profile may illustrate a relative brightness of the respective image region (e.g., the tabletop 362 and the aluminum filtration scale 352 described with respect to FIG. 4). A CsI detection profile of the tabletop may be compared to a CsI detection profile of the aluminum filtration scale to compute a CsI aluminum equivalence of the tabletop.

The first graph 510 shows a first plot 502 illustrating a CsI detection profile of the tabletop 362, and a second plot 504 illustrating a CsI detection profile of the aluminum filtration scale 352. As described above, the pixel value is plotted along the x-axis. The pixel value may be equivalent to a longitudinal position in the X-ray image. For example, with reference to FIG. 4, the pixel value may be a position in the annotated X-ray image 400 along the z-axis. A lower pixel value may be a position closer to a first side 424 of the annotated X-ray image 400, and a higher pixel value may be a position closer to a second side 426 of the annotated X-ray image 400, opposite the first side 424. For example, a first region 508 encompassing pixel values between 200 and 300 corresponds to a first region 428 of the annotated X-ray image 400 (e.g., including the sixth step 332 and a fifth step 334 of the aluminum filtration scale 352, and a corresponding region of the tabletop 362). A second region 518 encompassing pixel values between 300 and 400 corresponds to a second region 430 of the annotated X-ray image 400 (e.g., including the fifth step 334 and a fourth step 336 of the aluminum filtration scale 352, and a corresponding region of the tabletop 362).

The second plot 504 includes a series of stepwise increases in CsI profile of the aluminum filtration scale 352 that correspond to each step of the series of aluminum steps. For example, a first plateau 506 of the second plot 504 between approximately 160 pixels and 270 pixels illustrates a quality of the X-ray beam detected by the CsI scintillator in the first region of the first step 326, where the first step 326 has the first thickness. The first thickness may be equal to 1.0 mm, such as in the embodiment described herein. As the thickness decreases in the aluminum filtration scale 352, the brightness (e.g., the CsI value of the second plot 504) increases. The first plot 502 has a dome-like shape, which is also partially visible in the second plot 504 on either end of the series of stepwise increases. CsI values of the first plot 502 between approximately 200 pixels and 800 pixels are equal to approximately 240 photons, illustrating a near uniform brightness for the tabletop 362. The dome-like shape of each of the first plot 502 and the second plot 504 may be an effect of scattered radiation. Correction of the CsI scintillator detection profiles of each of the tabletop 362 and of the aluminum filtration scale 352 may include scatter correction, as further described herein.

The first plot 502 and the second plot 504 of the first graph 510 intersect between 100 and 200 pixels, which is in the region of the first step 326 of the aluminum filtration scale 352. Therefore, an initial observation may be that the CsI aluminum equivalence of the tabletop is equal to the thickness of the first step 326 of the aluminum filtration scale 352. The CsI detection profile of the tabletop 362 and the CsI detection profile of the aluminum filtration scale 352 are not directly comparable however, as a CsI scintillator response may vary among materials through which the irradiating beam is transmitted prior to reaching the detector 206. When the X-ray beam passes through each step of the series of steps of the aluminum filtration scale 352 (e.g., transmission of the X-ray beam through aluminum), a quality of the X-ray beam is changed, which affects how the X-ray beam is received by the detector 206. The quality of the X-ray beam is also changed when the X-ray beam passes through the tabletop 362, due to attenuation of the X-ray beam by the tabletop 362. Additionally, the CsI scintillator may not operate as a dosimeter, that is, the CsI scintillator may not directly measure a dose of ionizing radiation absorbed by the tabletop 362 or by each step of the series of steps of the aluminum filtration scale 352. Therefore, measuring an equivalent aluminum filtration of the tabletop 362 demands correction of each of the CsI detection profile of the tabletop 362 and the CsI detection profile of the aluminum filtration scale 352.

The type of material that the irradiating beams pass through on the path to the detector may change the quality of the irradiating beams differently. Therefore, correcting each of the CsI detection profiles for the tabletop 362 (e.g., formed of foam and carbon fiber) and for the aluminum filtration scale 352 (e.g., formed of aluminum) includes applying conversion factors having different values to each CsI detection profile. The second graph 520 of the first series of graphs 500 shows a first series of data points 512 illustrating conversion factor values for different thicknesses of carbon, and a second series of data points 514 illustrating conversion factor values for different thicknesses of aluminum. Thickness in millimeters (mm) is shown on the x-axis, and a relative conversion factor value is shown on the y-axis. For the first series of data points 512, the thickness is equal to the thickness of a carbon fiber skin that surrounds a foam core of the tabletop 362. For example, the foam core may have a thickness of 38 mm, and the foam core may be surrounded on either side (e.g., a first side in face-sharing contact with the aluminum filtration measurement tool 350 and a second side in face-sharing contact with the detector 206) by a 1 mm carbon fiber skin, such that a thickness of the tabletop 362 is 2 mm. For the second series of data points 514, the thickness is equal to a thickness of a respective aluminum step of the series of aluminum steps of the aluminum filtration scale 352.

Air kinetic energy released per unit mass (KERMA) is a sum of initial kinetic energies of all charged particles liberated by uncharged ionizing radiation in a sample of matter, divided by the mass of the sample. Described another way, air KERMA provides a measure of radiation dose in air. Air KERMA values of the tabletop 362 and each step of the series of aluminum steps of the aluminum filtration scale 352 may be directly compared to deduce an equivalent aluminum filtration of the tabletop 362, since a way that the measurement of radiation dose in air is detected may not be influenced by the material the radiation passes through prior to detection.

The conversion factors may be identified using simulations of X-ray photon paths through matter. For example, a Geant4 simulation may be performed using characteristics of the imaging system 200, the tabletop 362, and the aluminum filtration measurement tool 350 to simulate and compare filtration of photons by the tabletop 362 and by the aluminum filtration scale 352. For each photon emitted by irradiating beams of the vertical X-ray tube 204, a path of the photon through matter (e.g., the tabletop 362, the aluminum filtration measurement tool 350) is simulated to determine whether or not the photon reaches the detector 206. Material characteristics of the tabletop 362 and the aluminum filtration measurement tool 350 in the simulation are as described herein: the tabletop 362 formed of 38 mm foam with 2 mm carbon fiber skin; aluminum steps of the aluminum filtration measurement tool 350 made of equidistant steps with thicknesses of 0.4, 0.5, 0.6, 0.7, 0.8, 0.85, 0.9, and 1.0 mm; and thickness of the first planar surface 310, the second planar surface 312, and the vertical wall 358 equal to 3 mm. A design of experiment of the simulation is run to assess respective effects of foam density and carbon fiber thickness on photon absorption/transmission. Variables of the simulation may include foam density and carbon thickness. Simulations run to generate the air KERMA profile of the tabletop 362 simulate a detector made of pure air, instead of a detector including a CsI scintillator, to remove influence of how CsI scintillator response may vary among materials from the resulting profile. A simulation profile of each of the tabletop 362 and the aluminum filtration measurement tool 350 may include a ratio of primary photons to scatter photons detected by the detector (e.g., the pure air detector or the detector including the CsI scintillator). By comparing primary photon and scatter photon ratios of the CsI profile for the tabletop 362 and the simulated air KERMA response for the tabletop 362, conversion factors are identified that may be used to correct the CsI profile for the tabletop 362 to the simulated air KERMA response for the tabletop 362. These identified conversion factors may be used to correct experimental measurements of the CsI profile for the tabletop 362 (e.g., the first plot 502 of the first graph 510) to acquire the air KERMA response for the tabletop (e.g., the first profile of a third graph 530).

The third graph 530 of the first series of graphs 500 shows a first plot 532 illustrating an air KERMA profile of the tabletop 362, and a second plot 534 illustrating an air KERMA profile of the aluminum filtration scale 352. The air KERMA profiles are generated by applying respective conversion factors (e.g., from the second graph 520) to the CsI detection profile of the tabletop 362 and the CsI detection profile of the aluminum filtration scale 352 (e.g., from the first graph 510). For example, the first plot 532 of the third graph 530 may be acquired by applying conversion factors from the first series of data points 512 of the second graph 520 to the first plot 502 of the first graph 510. The second plot 534 of the third graph 530 may be acquired by applying respective conversion factors from the second series of data points 514 of the second graph 520 to the second plot 504 of the first graph 510 to compute the air KERMA of the aluminum filtration scale. An air KERMA value is plotted along the y-axis, and a pixel value (e.g., a position in the X-ray image) is plotted along the x-axis. Similar to the first plot 502 of the first graph 510, the first plot 532 of the third graph 530 has a dome-like shape. Additionally, similar to the second plot 504 of the first graph 510, the second plot 534 of the third graph 530 includes a series of stepwise increases in the air KERMA profile that correspond to each step of the series of aluminum steps, and a dome-like shape on either end of the series of the stepwise increases. The dome-like shape of each of the first plot 532 and the second plot 534 may be an effect of scattered radiation, which may be corrected using scatter correction as further described herein with respect to FIGS. 6-7.

An appropriate conversion factor of the first series of data points 512 to apply to the CsI detection profile of the tabletop 362 (e.g., shown in the first plot 502 of the first graph 510) may be unknown. Simulations may be performed to identify a conversion factor for the CsI detection profile of the tabletop 362. For example, a desired aluminum filtration equivalence of the tabletop 362 may be equal to filtering provided by aluminum having a known thickness between 0.6 mm and 0.7 mm. The second graph 520 includes relative conversion factors for desired aluminum filtration in the second series of data points 512, where application of a relative conversion factor to a corresponding aluminum thickness value provides a corrected aluminum filtration value for the given aluminum thickness, as shown in the third graph 530, compared to the first graph 510. As described above, appropriate conversion factors that may be applied to the first plot 502 of the first graph 510 to achieve a similarly corrected tabletop filtration (e.g., compared to correction of the desired aluminum filtration) may be unknown. A conversion factor may be chosen from the first series of data points 512, shown in the second graph 520, that provides a systematic overestimation of the aluminum equivalence. For example, a conversion factor value of the first series of data points 512 that is between the thickness of 0.6 mm and 0.7 mm may be selected, as the conversion factor for the second series of data points 514 between the thickness of 0.6 mm and 0.7 mm provides desired correction of the aluminum filtration. As shown in the third graph 530 of FIG. 5, the first plot 532 and the second plot 534 intersect at an aluminum step thickness between 0.6 mm and 0.7 mm. The selected conversion factors for the first series of data points 512 and the second series of data points 514 therefore correct the first plot 502 and the second plot 504 to provide the first plot 532 and the second plot 534, respectively, as shown in the third graph 530.

Turning to FIG. 6, a graph 600 is shown of a scatter photon to primary photon ratio of the tabletop 362 that may be used in scatter correction of the CsI detection profile of the tabletop 362. The graph 600 includes scatter to primary photon ratios for different tabletop thicknesses. Data are obtained from global average values of the tabletop window 354. Most of the scattered variability is the result of a thickness of the carbon fiber skin, and foam density has less of an impact on scattered variability. The scatter photon to primary photon ratio of the tabletop as shown in the graph 600 may be used to correct the scatter of the CsI aluminum equivalence of the tabletop, as further described herein.

A first plot 602 of the graph 600 illustrates a scatter to primary photon ratio of the tabletop with a carbon skin thickness of 1.5 mm. A second plot 604 of the graph 600 illustrates a scatter to primary photon ratio of the tabletop with a carbon skin thickness of 1.95 mm. The scatter to primary ratio is shown along the y-axis as a percentage, and an apparent equivalent aluminum filtration of the tabletop, from CsI detector data, is shown along the x-axis in millimeters. Each of the first plot 602 and the second plot 604 increase linearly, where the scatter to primary photon ratio increases as the apparent equivalent aluminum filtration thickness increases.

In reality, primary and scatter signals of the tabletop 362 are unknown. Scatter of the tabletop may be estimated from the apparent equivalent aluminum filtration of the total brightness signal of the tabletop. For example, the apparent equivalent aluminum filtration is obtained by interpolation of the primary aluminum CsI signal to a total tabletop signal. The scatter to primary photon ratio (SPR) of the tabletop, provided by the simulation, may be used as a function of the apparent equivalent aluminum filtration. A primary signal under the tabletop may then be computed. For example, the SPR of the tabletop is shown as a dashed line 606 in the graph 600. The dashed line 606 intersects the first plot 602 and the second plot 604 at the primary signal for the respective tabletop thickness, as indicated by an arrow 608. A true scatter fraction of the tabletop may be obtained from the apparent equivalent aluminum filtration thickness in this way by deducing the scatter fraction from the total signal.

Turning to FIG. 7, a graph 700 shows an effect of a scatter point spread function (ScPSF) of corresponding aluminum step thicknesses. A shape of a scatter signal is deduced from integration of the ScPSF over the irradiated area. As described with respect to FIG. 5, CsI detector profiles of the tabletop 362 and of the aluminum filtration scale 352 have dome-like shapes due to influence of scatter photons. An aluminum step thickness in millimeters is shown along the x-axis, and a fraction of total scatter signal in each tabletop region of interest is shown along the y-axis. The graph 700 includes multiple plots 710, each of which illustrates a run of the simulation where each run has a different foam thickness and/or carbon fiber skin thickness, as shown in the table 702. The distribution of total scattered signal in each tabletop region of interest (e.g., corresponding to an aluminum step of the series of aluminum steps) is deduced from a convolution operation that provides a scattered signal shape over an irradiated area (e.g., the tabletop 362 exposed via the tabletop window 354). As described with respect to FIGS. 10A-10B, the ScPCF and the SPR of the tabletop may be used in scatter correction of the CsI detector profile of the tabletop (e.g., shown in FIG. 5).

FIG. 8 shows a graph 800 illustrating a CsI detector profile to air KERMA conversion factor ratio as determined using simulations and measurements. The graph 800 may be used to identify an appropriate conversion factor to be used to convert the CsI detector profile of the tabletop to the air KERMA of the tabletop. An aluminum thickness or equivalent aluminum thickness in millimeters is shown on the x-axis. The y-axis shows a relative conversion factor, and a corresponding brightness (e.g., of the aluminum scale and/or the tabletop). A first plot 802 shows simulated values of a carbon (e.g., of the carbon fiber skin of the tabletop) X-ray beam quality. A second plot 804 shows simulated aluminum (e.g., of the aluminum filtration scale) X-ray beam quality. A third plot 806 shows a measured conversion factor of the tabletop, and a fourth plot 808 shows a measured conversion factor of the aluminum scale. As described above, the conversion factors may be generated from simulations comparing CsI detector profiles of each of the tabletop and the aluminum scale to respective air KERMA values, and deducing the conversion factor.

FIG. 9 shows a graph 900 illustrating a first plot 902 of aluminum scale air KERMA, and a second plot 904 of tabletop air KERMA. The first plot 902 and the second plot 904 are illustrated as ratios of air KERMA to aluminum thickness, and an intersection of the first plot 902 and the second plot 904 at approximately 0.8 mm Al provides the air equivalent aluminum filtration of the tabletop.

The method for measuring the air equivalent aluminum filtration of the tabletop is now described with respect to FIGS. 10A-10B and with reference to FIGS. 1-9. Briefly, the method comprises acquiring a single X-ray image of a tabletop and an aluminum filtration scale captured using an X-ray detector (e.g., a CsI scintillator detector), identifying a brightness of the tabletop and a brightness of the aluminum filtration scale in the single X-ray image, computing an aluminum equivalence of the tabletop, converting the brightness of the aluminum filtration scale to an air KERMA of the aluminum filtration scale and converting the aluminum equivalence of the tabletop to an air KERMA of the tabletop, and comparing the air KERMA of the tabletop to the air KERMA of the aluminum filtration scale to identify an air equivalent aluminum filtration of the tabletop. Further details of the method are provided in the description of FIGS. 10A-10B. The method is described with respect to FIGS. 10A-10B in the context of an X-ray detector configured as a CsI scintillator detector, thus equivalence of the tabletop may be referred to as CsI equivalence of the tabletop. In other examples where other types of X-ray detectors may be used, the equivalence of the tabletop may be determined using the method described herein, and using different coefficients of calculation (e.g., conversion factors)

that are relative to the X-ray detector type, and which may be determined using methods similar to those described herein.

FIGS. 10A-10B show a flow chart of a method 1000 for measuring an equivalent aluminum filtration of a tabletop using an X-ray imaging system. The X-ray imaging system that stores and executes the method 1000 may be configured as a manufacturing and quality control X-ray imaging system. Described another way, the X-ray system that executes the method 1000 may not be a medical X-ray imaging system configured to capture X-ray images of patients or other imaging subjects for image analysis purposes. The X-ray imaging system may be similar to, or the same as, the X-ray imaging system 200 of FIG. 2. As described herein, the method 1000 is used to measure an equivalent aluminum filtration of a tabletop, or a section of the tabletop. The tabletop may be an example of a tabletop that is used in medical X-ray imaging systems to position a patient or other imaging subject, such as the support surface 138 of the medical imaging system 100 of FIG. 1. Instructions for carrying out the method 1000 may be executed by a controller (e.g., electronic controller 216 described above with reference to FIG. 2) based on instructions stored on a memory of the controller and in conjunction with signals received from sensors of the imaging system, such as the detector 206 described above with reference to FIG. 2.

Beginning at FIG. 10A, at 1002, the method 1000 includes acquiring a single X-ray image of the tabletop and the aluminum filtration scale. For example, the single X-ray image (herein, "the X-ray image") includes visualizations of both the tabletop and the aluminum filtration scale. As described with respect to FIGS. 3A-4, the tabletop is positioned on the detector, and the aluminum filtration measurement tool is positioned in part on the tabletop and in part on the detector, such that a portion of the tabletop is exposed to air through the tabletop window, and the aluminum filtration scale is positioned on the detector. For example, the first planar surface of the aluminum filtration measurement tool is in face-sharing contact with the tabletop, and the second planar surface is in face-sharing contact with the detector of the X-ray imaging system. Capturing the X-ray image includes, at 1004, simultaneously exposing the tabletop and the aluminum filtration scale to X-ray beams. The aluminum filtration tool acts to shield the tabletop, except for a portion of the tabletop exposed via the tabletop window, from the X-ray beams. X-ray beams pass through the exposed portion of the tabletop and into the CsI scintillator and the detector of the X-ray imaging system, as described with respect to FIGS. 1-2. Further, X-ray beams pass through and are filtered by the aluminum filtration scale of the aluminum filtration tool, and into the detector of the X-ray imaging system. Thus, the X-ray image of the tabletop and the aluminum filtration scale is captured. For example, the X-ray image may be the X-ray image 400 shown and described with respect to FIG. 4. As described herein, characteristics of the irradiating beams, such as a beam strength, may be changed by material properties of the tabletop.

At 1006, the method 1000 includes identifying a location of the tabletop window and a location of the aluminum filtration scale in the X-ray image captured at 1002. The location of the tabletop window and the location of the aluminum filtration scale may be automatically identified by applying a filter, such as a Canny filter or other edge detection filter, to the X-ray image. The filter may locate and identify the tabletop window and the aluminum filtration scale, and may provide a filtered image, an annotated X-ray image, and/or pixel coordinate locations in the image identifying each location.

At 1008, the method 1000 includes splitting the aluminum filtration scale image (e.g., the portion of the X-ray image identified as the location of the aluminum filtration scale) into aluminum steps. As described with respect to FIGS. 3A-4, the aluminum filtration scale comprises multiple aluminum steps having different aluminum thicknesses. The different aluminum thicknesses of the multiple aluminum steps may filter the X-ray beams by different amounts, and thus a brightness of each aluminum step captured in the X-ray image may be different. Splitting the aluminum filtration scale image into the multiple aluminum steps may include, at 1010, applying a Sobel filter to the X-ray image. The Sobel filter may be applied horizontally to the X-ray image (e.g., such that Sobel projection lines are parallel with the center line 314 of the aluminum filtration measurement tool 350 of FIGS. 3A-4). Splitting the aluminum filtration scale image may further include, at 1012, identifying peaks at relevant locations in the aluminum filtration scale image using the Sobel filter, and identifying tolerance of peak locations to acquire non-adjacent step locations. For example, peaks may be identified between each aluminum step, and may be used to deduce borders (e.g., a left edge and a right edge) of each aluminum step, where the borders are parallel to the center line 314 of the aluminum filtration measurement tool 350.

At 1014, the method 1000 includes computing an average brightness of each aluminum step from the X-ray image, excluding signals greater than 2.5 sigma from the average brightness. The average brightness of each aluminum step may represent a strength of the X-ray beams after being filtered by the respective aluminum step thickness. The average brightness of an aluminum step may be, for example, an average row signal provided by the detector. Calculating the average brightness of each aluminum step may include: calculating an initial average brightness using all brightness values of the given aluminum step, identifying brightness values greater than 2.5 sigma from the initial average brightness, and recalculating the average brightness of the aluminum step by excluding the brightness values identified as being greater than 2.5 sigma from the recalculated average brightness. An example flow chart of a method for calculating average brightness of a step, excluding brightness values greater than 2.5 sigma from the initial average brightness, is described with respect to calculating average tabletop brightness in FIG. 11, and may be similarly applied to calculating average brightness of each aluminum step.

At 1016, the method 1000 includes subtracting a scatter fraction from the average brightness of each aluminum step. As described with respect to FIGS. 5-7, photons of the X-ray beam may be scattered during filtration and transmission through each aluminum step of the series of aluminum steps. The scatter fraction of each aluminum step may be identified using simulations, such as Geant4 simulations. The scatter fraction may be subtracted from the average brightness of the respective aluminum step to acquire a primary photon measurement of each aluminum step.

At 1018, the method 1000 includes computing an average brightness of the tabletop window excluding signals greater than 2.5 sigma from the average brightness. The average brightness of the tabletop window may represent a strength of the X-ray beams after being filtered by the tabletop (e.g., the carbon fiber skin and the foam). The average brightness of the tabletop window may be, for example, an average signal provided by the detector. As described with respect to operation 1014 and further described with respect to operation 1024 and FIG. 11, calculating the average brightness of the tabletop may include identifying and excluding signals greater than 2.5 sigma from the average brightness to assist in reducing scatter effects and thus increasing accuracy of equivalence determination.

At 1020, the method 1000 includes computing an equivalence of the tabletop from the X-ray image. As briefly described above, the detector of the X-ray imaging system may include a CsI scintillator that converts received X-ray beams to visible light. Computing a CsI equivalence of the tabletop may include, at 1022, identifying steps of the tabletop window. Neither the tabletop window nor the tabletop itself may be physically divided into steps, the image of the tabletop in the X-ray image may be divided into steps to assist in data organization and processing. For example, a size (e.g., a height) of adjacent aluminum steps may be translated to the tabletop to divide the tabletop into the same number of steps as the aluminum filtration scale. Computing the CsI equivalence of the tabletop may further include, at 1024, calculating an average brightness excluding tabletop brightness signals distant by more than 2.5 sigma of the average brightness value. Further details regarding exclusion of tabletop brightness signals distant by more than 2.5 sigma of the average brightness value are described with respect to FIG. 11.

Turning briefly to FIG. 11, a method 1100 is shown for performing an iterative cleanup of individual pixels of the tabletop window in the X-ray image. For example, an average tabletop step brightness may be computed for each tabletop step identified at 1022. As briefly described with respect to FIGS. 5-7, scatter photons from the X-ray beam may cause unequal distribution, where a brightness is weaker around a perimeter of the tabletop window. Brightness of the tabletop at a single tabletop step may not be representative of total filtration by the tabletop. Therefore, brightness values distant by more than 2.5 sigma of the average value are removed from a total tabletop brightness calculation. Removed brightness values are not retained for average computations, as described herein with respect to the method 1000. A threshold distance above which brightness signals are removed may be configurable. In the example described herein, the threshold distance is 2.5 sigma from the average brightness value. In other examples, the threshold distance may be greater than or less than 2.5 sigma from the average brightness value.

At 1102, the method 1100 includes identifying a first region of interest (i) in the tabletop window. As described with respect to operation 1022 of the method 1000, the first region of interest may be a step of the tabletop window. For example, the step of the tabletop window may be a section of the tabletop window within the first region 428, as described with respect to FIGS. 4-5.

At 1104, the method 1100 includes calculating an average brightness of the first region of interest. As described herein, photons of the X-ray beam may be scattered during filtration and transmission through the tabletop. The average brightness of the tabletop window may be, for example, an average of signals provided by the detector.

At 1106, the method 1100 includes calculating a standard deviation of the region of interest. Calculating the standard deviation may include calculating the standard deviation of brightness values used to calculate the average brightness at operation 1104.

At 1108, the method 1100 includes performing a count of pixels to identify a brightness values that are distant by more than 2.5 sigma of the average value (e.g., the average brightness of the first region of interest, calculated at operation 1104). Performing the count of pixels includes calculating an absolute value of a difference of individual pixel (p) values for each pixel (e.g., p(n), p(n+1), etc.) and the average value (M(i)), and identifying values that are greater than a product of 2.5 (e.g., sigma value) and the standard deviation value (S(i)). The count of pixels may be performed as shown in equation 1:

$$|p(n)-M(i)|>2.5*S(i) \qquad (1).$$

At 1110, the method 1100 includes determining if there are more than zero pixels in the region of interest that have a brightness value distant by more than 2.5 sigma of the average value. If there are greater than zero pixels in the region of interest (e.g., if one or more pixels in the region of interest) has a brightness value that distant by more than 2.5 sigma of the average value), the method proceeds to 1112.

At 1112, the method 1100 includes excluding pixels identified as having brightness values distant by more than 2.5 sigma of the average value from a total tabletop brightness calculation. This may include generating a brightness value dataset to be used in further calculations, as further described herein, where the brightness value dataset includes pixels having brightness values that are distant by less than 2.5 sigma of the average value.

Returning briefly to operation 1110, if it is determined there are not greater than zero pixels in the region of interest with a brightness value distant by more than 2.5 sigma of the average value, the method 1100 proceeds to operation 1114. At operation 1114, the method 1100 includes calculating an average total tabletop brightness. As described with respect to operation 1112, the average total tabletop brightness may be calculated from a dataset, such as the brightness value dataset, that includes pixels having brightness values that are distant by less than 2.5 sigma of the average value.

The method 1100 may be repeated for each region of interest of the tabletop window. In this way, a dataset of pixels and respective brightness thereof that are used to calculate the average total tabletop brightness may be iteratively "cleaned", such that some pixels may be excluded from the dataset and not retained for average computations, based on a relative brightness value.

The method 1000 continues in FIG. 10B. At 1026, the method 1000 includes deducing a global scatter fraction of the tabletop using the equivalence of the tabletop (e.g., computed at 1020). As described with respect to FIGS. 5-7, a total scatter to primary photon ratio may be unknown for the tabletop, and a global scatter fraction may be estimated using simulations.

At 1028, the method 1000 includes computing a scatter profile of the tabletop from the scatter fraction of the tabletop. Computing the scatter profile of the tabletop includes, at 1030, deducing a fraction of the scatter profile at each tabletop step. At 1032, the method 1000 includes subtracting the scatter fraction of each tabletop step from the respective tabletop step brightness.

At 1034, the method 1000 includes converting the brightness of each aluminum step and the brightness of each tabletop step to air KERMA values using respective conversion factors. As described herein with respect to FIGS. 5-9, the conversion factor may be identified using simulations and comparisons of aluminum filtration (e.g., from the aluminum filtration scale) in air (e.g., air KERMA of the aluminum filtration scale) and as detected by the CsI scintillator (e.g., CsI aluminum equivalence of the tabletop).

At 1036, the method 1000 includes computing an air equivalent aluminum filtration value of the tabletop by finding an intersection of the tabletop filtration and the aluminum step filtration, using the air KERMA values. As described with respect to FIG. 9, the air equivalent aluminum filtration value of the tabletop provides a relative filtering provided by the tabletop in terms of aluminum filtering.

At 1038, the method 1000 includes determining whether the air equivalent aluminum filtration of the tabletop is less than a threshold filtration value. The threshold filtration value may be, for example, 0.80 mm Al. When the air equivalent aluminum filtration of the tabletop is less than the threshold filtration value, the tabletop may provide at least a desired amount of filtering. When the air equivalent aluminum filtration of the tabletop is equal to or greater than the threshold filtration value, the tabletop may provide more than a desired amount of filtering. If the air equivalent aluminum filtration value of the tabletop is less than the threshold filtration value, the method 1000 proceeds to 1040.

At 1040, the method 1000 include outputting a "pass" indicator and two flanking aluminum step thicknesses for display, as well as storing results of the method 1000. For example, the "pass" indicator may be a text-based message, a graphic, a color indicator, and so on. The results of the method 1000 that are stored may include values used to calculate the air equivalent aluminum filtration value of the tabletop, including locations of the aluminum steps of the aluminum filtration scale, locations of regions of interest of the tabletop, CsI detector profiles for the aluminum filtration scale and the tabletop, scatter factors and other scatter ratios, and air KERMA values of the tabletop and the aluminum filtration scale.

If the air equivalent aluminum filtration value of the tabletop is not less than the threshold filtration value at 1038, the method 1000 proceeds to 1042. At 1042, the method 1000 includes outputting a "fail" indicator and two flanking aluminum step thicknesses for display, as well as storing results of the method 1000. For example, the "fail" indicator may be a text-based message, a graphic, a color indicator, and so on.

After either 1040 or 1042, method 1000 may end.

In this way, the method and systems described herein address expected impending obsolescence of current radiographic methods and continuously increasing cost of radiographic material (film, development chemical products). In addition, the methods and systems described herein will decrease resource demand, since it provides a final performance from a single digital X-ray image instead of human readout of a developed radiographic film. The systems and methods described herein provides the tabletop value faster than may be acquired using radiographic film development, and has the potential to reduce errors from human interpretation of radiographic film by a repeatable software analysis of a digital image.

The disclosure also provides support for a method for an X-ray system, comprising: acquiring a single X-ray image of a tabletop and an aluminum filtration scale using a detector, identifying a brightness of the tabletop and a brightness of the aluminum filtration scale in the single X-ray image, computing an aluminum equivalence of the tabletop, converting the brightness of the aluminum filtration scale to an air kinetic energy released per unit mass (KERMA) of the aluminum filtration scale and converting the aluminum equivalence of the tabletop to an air KERMA of the tabletop, and comparing the air KERMA of the tabletop to the air KERMA of the aluminum filtration scale to identify an air equivalent aluminum filtration of the tabletop. In a first example of the method, the single X-ray image is acquired using a cesium iodide (CsI) scintillator detector. In a second example of the method, optionally including the first example, the method further comprises: deducing a global scatter of the tabletop, and subtracting the global scatter of the tabletop from the aluminum equivalence of the tabletop. In a third example of the method, optionally including one or both of the first and second examples, converting the brightness of the aluminum filtration scale to the air KERMA of the aluminum filtration scale comprises applying a first conversion factor to the brightness of the aluminum filtration scale, and converting the aluminum equivalence of the tabletop the air KERMA of the aluminum equivalence comprises applying a second conversion factor, different from the first conversion factor, to the aluminum equivalence of the tabletop. In a fourth example of the method, optionally including one or more or each of the first through third examples, the aluminum filtration scale comprises a series of aluminum steps that each have a different aluminum thickness, and identifying the brightness of the aluminum filtration scale comprises identifying an average brightness of each aluminum step of the series of aluminum steps. In a fifth example of the method, optionally including one or more or each of the first through fourth examples, the method further comprises: deducing a step scatter of each step of the series of aluminum steps, and subtracting a respective step scatter from the average brightness of each aluminum step. In a sixth example of the method, optionally including one or more or each of the first through fifth examples, converting the brightness of the aluminum filtration scale to the air KERMA of the aluminum filtration scale comprises converting the average brightness of each aluminum step to an air KERMA of each aluminum step. In a seventh example of the method, optionally including one or more or each of the first through sixth examples, identifying the air equivalent aluminum filtration of the tabletop comprises comparing the air KERMA of the tabletop to the air KERMA of each aluminum step, and identifying a thickness of an aluminum step of the series of aluminum steps having an air KERMA value that is equal to the air KERMA of the tabletop. In an eighth example of the method, optionally including one or more or each of the first through seventh examples, the method further comprises, determining if the air equivalent aluminum filtration of the tabletop is less than a threshold filtration and, in response to the air equivalent aluminum filtration of the tabletop being less than the threshold filtration, outputting a "pass" indicator, values of two flanking aluminum step thicknesses, and storing results of the method in memory.

The disclosure also provides support for an X-ray imaging system, comprising: an X-ray tube, a detector, an aluminum filtration measurement tool having a tabletop window and an aluminum filtration scale, and a controller with computer-readable instructions stored on non-transitory memory that, when executed, cause the controller to: acquire a single X-ray image in a single scan of a tabletop, positioned on the detector, and the aluminum filtration measurement tool, where the aluminum filtration measurement tool is positioned in part on the tabletop and in part on the detector, such that a portion of the tabletop is exposed to air through the tabletop window, and the aluminum filtration scale is positioned on the detector, identify, in the single X-ray image, a brightness of the portion of the tabletop exposed to air and a brightness of the aluminum filtration scale, compute an aluminum equivalence of the portion of the tabletop exposed to air, scatter correct the aluminum equivalence of the portion of the tabletop exposed to air and the brightness of the aluminum filtration scale, convert a scatter-corrected aluminum equivalence of the portion of the tabletop exposed to air and a scatter-corrected brightness of the aluminum filtration scale to an air KERMA of the tabletop and an air KERMA of the aluminum filtration scale, respectively, and compare the air KERMA of the tabletop and the air KERMA of the aluminum filtration scale to identify an air equivalent aluminum filtration of the tabletop. In a first example of the system, the X-ray tube directs X-ray beams orthogonal to the tabletop and the aluminum filtration scale. In a second example of the system, optionally including the first example, the tabletop and the aluminum filtration scale are irradiated by X-ray beams from the X-ray tube that provide a half-value layer of greater than 3.6 aluminum equivalence for 100 kilovolts peak X-ray beam. In a third example of the system, optionally including one or both of the first and second examples, the aluminum filtration scale comprises a series of aluminum steps arranged in parallel along a length of the aluminum filtration scale, and each step of the series of aluminum steps has a different aluminum thickness from other steps of the series of aluminum steps. In a fourth example of the system, optionally including one or more or each of the first through third examples, the aluminum filtration measurement tool comprises: a first planar surface having the tabletop window extending through a thickness of the first planar surface, a second planar surface having an aluminum scale window extending through a thickness of the second planar surface, the second planar surface offset from and coupled to the first planar surface by a vertical wall, the vertical wall perpendicular to the first planar surface to the second planar surface, and the aluminum filtration scale positioned in the aluminum scale window. In a fifth example of the system, optionally including one or more or each of the first through fourth examples, the first planar surface is elevated above the second planar surface by a height of the vertical wall. In a sixth example of the system, optionally including one or more or each of the first through fifth examples, the aluminum filtration measurement tool is formed of lead and carbon.

The disclosure also provides support for a method for an X-ray imaging system, comprising: simultaneously irradiating a tabletop and an aluminum filtration scale having a series of aluminum steps with different thicknesses using an X-ray beam, capturing photons filtered by tabletop and the aluminum filtration scale using a cesium iodide (CsI) scintillator detector, generating an X-ray image from captured photons, identifying a brightness of the tabletop and each step of the series of steps of the aluminum filtration scale in the X-ray image, computing a CsI aluminum equivalence of the tabletop, computing global scatter for the tabletop, subtracting scatter from the brightness of the tabletop and from each step of the series of steps of the aluminum filtration scale to generate a scatter-free brightness value of the tabletop and a scatter-free brightness value of each step of the aluminum filtration scale, converting the scatter-free brightness value of the tabletop and the scatter-free brightness value of each step of the aluminum filtration scale to a tabletop air KERMA value and a series of aluminum step air KERMA values, respectively, by applying a conversion factor to each, comparing the tabletop air KERMA value to the series of aluminum step air KERMA values to identify an air equivalent aluminum filtration of the tabletop, and storing the air equivalent aluminum filtration of the tabletop in memory and outputting the air equivalent aluminum filtration of the tabletop for display on a display device. In a first example of the method, identifying the brightness of the tabletop comprises: locating the tabletop, and defining individual regions of interest of the tabletop using the series of aluminum steps of the aluminum filtration scale, wherein each region of interest of the tabletop is parallel to an aluminum step of the series of aluminum steps. In a second example of the method, optionally including the first example, computing the CsI aluminum equivalence of the tabletop comprises comparing a brightness of each region of interest of the tabletop to the brightness of each step of the series of aluminum steps. In a third example of the method, optionally including one or both of the first and second examples, a first conversion factor is applied to the scatter-free brightness value of the tabletop and a second conversion factor, different from the first conversion factor, is applied to the scatter-free brightness value of each step of the aluminum filtration scale.

As used herein, the term "approximately" is construed to mean plus or minus five percent of the range unless otherwise specified.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an X-ray system, comprising:
acquiring a single X-ray image of a tabletop and an aluminum filtration scale using a detector;
identifying a brightness of the tabletop and a brightness of the aluminum filtration scale in the single X-ray image;
computing an aluminum equivalence of the tabletop;
converting the brightness of the aluminum filtration scale to an air kinetic energy released per unit mass (KERMA) of the aluminum filtration scale and converting the aluminum equivalence of the tabletop to an air KERMA of the tabletop; and
comparing the air KERMA of the tabletop to the air KERMA of the aluminum filtration scale to identify an air equivalent aluminum filtration of the tabletop.

2. The method of claim 1, wherein the single X-ray image is acquired using a cesium iodide (CsI) scintillator detector.

3. The method of claim 1, further comprising deducing a global scatter of the tabletop, and subtracting the global scatter of the tabletop from the aluminum equivalence of the tabletop.

4. The method of claim 1, wherein converting the brightness of the aluminum filtration scale to the air KERMA of the aluminum filtration scale comprises applying a first conversion factor to the brightness of the aluminum filtration scale, and converting the aluminum equivalence of the tabletop the air KERMA of the aluminum equivalence comprises applying a second conversion factor, different from the first conversion factor, to the aluminum equivalence of the tabletop.

5. The method of claim 1, wherein the aluminum filtration scale comprises a series of aluminum steps that each have a different aluminum thickness, and identifying the brightness of the aluminum filtration scale comprises identifying an average brightness of each aluminum step of the series of aluminum steps.

6. The method of claim 5, further comprising deducing a step scatter of each step of the series of aluminum steps, and subtracting a respective step scatter from the average brightness of each aluminum step.

7. The method of claim 6, wherein converting the brightness of the aluminum filtration scale to the air KERMA of the aluminum filtration scale comprises converting the average brightness of each aluminum step to an air KERMA of each aluminum step.

8. The method of claim 7, wherein identifying the air equivalent aluminum filtration of the tabletop comprises comparing the air KERMA of the tabletop to the air KERMA of each aluminum step, and identifying a thickness of an aluminum step of the series of aluminum steps having an air KERMA value that is equal to the air KERMA of the tabletop.

9. The method of claim 1, further comprising, determining if the air equivalent aluminum filtration of the tabletop is less than a threshold filtration and, in response to the air equivalent aluminum filtration of the tabletop being less than the threshold filtration, outputting a "pass" indicator, values of two flanking aluminum step thicknesses, and storing results of the method in memory.

10. An X-ray imaging system, comprising:
an X-ray tube;
a detector;
an aluminum filtration measurement tool having a tabletop window and an aluminum filtration scale; and
a controller with computer-readable instructions stored on non-transitory memory that, when executed, cause the controller to:
acquire a single X-ray image in a single scan of a tabletop, positioned on the detector, and the aluminum filtration measurement tool, where the aluminum filtration measurement tool is positioned in part on the tabletop and in part on the detector, such that a portion of the tabletop is exposed to air through the tabletop window, and the aluminum filtration scale is positioned on the detector;
identify, in the single X-ray image, a brightness of the portion of the tabletop exposed to air and a brightness of the aluminum filtration scale;
compute an aluminum equivalence of the portion of the tabletop exposed to air;
scatter correct the aluminum equivalence of the portion of the tabletop exposed to air and the brightness of the aluminum filtration scale;

convert a scatter-corrected aluminum equivalence of the portion of the tabletop exposed to air and a scatter-corrected brightness of the aluminum filtration scale to an air KERMA of the tabletop and an air KERMA of the aluminum filtration scale, respectively; and compare the air KERMA of the tabletop and the air KERMA of the aluminum filtration scale to identify an air equivalent aluminum filtration of the tabletop.

11. The X-ray imaging system of claim 10, wherein the X-ray tube directs X-ray beams orthogonal to the tabletop and the aluminum filtration scale.

12. The X-ray imaging system of claim 10, wherein the tabletop and the aluminum filtration scale are irradiated by X-ray beams from the X-ray tube that provide a half-value layer of greater than 3.6 aluminum equivalence for 100 kilovolts peak X-ray beam.

13. The X-ray imaging system of claim 10, wherein the aluminum filtration scale comprises a series of aluminum steps arranged in parallel along a length of the aluminum filtration scale, and each step of the series of aluminum steps has a different aluminum thickness from other steps of the series of aluminum steps.

14. The X-ray imaging system of claim 13, wherein the aluminum filtration measurement tool comprises:

a first planar surface having the tabletop window extending through a thickness of the first planar surface;

a second planar surface having an aluminum scale window extending through a thickness of the second planar surface, the second planar surface offset from and coupled to the first planar surface by a vertical wall, the vertical wall perpendicular to the first planar surface to the second planar surface; and the aluminum filtration scale positioned in the aluminum scale window.

15. The X-ray imaging system of claim 14, wherein the first planar surface is elevated above the second planar surface by a height of the vertical wall.

16. The X-ray imaging system of claim 10, wherein the aluminum filtration measurement tool is formed of lead and carbon.

17. A method for an X-ray imaging system, comprising:

simultaneously irradiating a tabletop and an aluminum filtration scale having a series of aluminum steps with different thicknesses using an X-ray beam;

capturing photons filtered by tabletop and the aluminum filtration scale using a cesium iodide (CsI) scintillator detector;

generating an X-ray image from captured photons;

identifying a brightness of the tabletop and each step of the series of steps of the aluminum filtration scale in the X-ray image;

computing a CsI aluminum equivalence of the tabletop;

computing global scatter for the tabletop;

subtracting scatter from the brightness of the tabletop and from each step of the series of steps of the aluminum filtration scale to generate a scatter-free brightness value of the tabletop and a scatter-free brightness value of each step of the aluminum filtration scale;

converting the scatter-free brightness value of the tabletop and the scatter-free brightness value of each step of the aluminum filtration scale to a tabletop air KERMA value and a series of aluminum step air KERMA values, respectively, by applying a conversion factor to each;

comparing the tabletop air KERMA value to the series of aluminum step air KERMA values to identify an air equivalent aluminum filtration of the tabletop; and storing the air equivalent aluminum filtration of the tabletop in memory and outputting the air equivalent aluminum filtration of the tabletop for display on a display device.

18. The method of claim 17, wherein identifying the brightness of the tabletop comprises:

locating the tabletop; and defining individual regions of interest of the tabletop using the series of aluminum steps of the aluminum filtration scale, wherein each region of interest of the tabletop is parallel to an aluminum step of the series of aluminum steps.

19. The method of claim 18, wherein computing the CsI aluminum equivalence of the tabletop comprises comparing a brightness of each region of interest of the tabletop to the brightness of each step of the series of aluminum steps.

20. The method of claim 17, wherein a first conversion factor is applied to the scatter-free brightness value of the tabletop and a second conversion factor, different from the first conversion factor, is applied to the scatter-free brightness value of each step of the aluminum filtration scale.

* * * * *